US009196035B2

(12) United States Patent
Weiss

(10) Patent No.: US 9,196,035 B2
(45) Date of Patent: *Nov. 24, 2015

(54) COMPUTER APPARATUS FOR IMAGE CREATION AND ANALYSIS

(71) Applicant: Kenneth L. Weiss, Jackson, MI (US)

(72) Inventor: Kenneth L. Weiss, Jackson, MI (US)

( * ) Notice: Subject to any disclaimer, the term of this patent is extended or adjusted under 35 U.S.C. 154(b) by 242 days.

This patent is subject to a terminal disclaimer.

(21) Appl. No.: 13/848,638

(22) Filed: Mar. 21, 2013

(65) Prior Publication Data

US 2013/0287276 A1   Oct. 31, 2013

Related U.S. Application Data

(63) Continuation of application No. 12/155,803, filed on Jun. 10, 2008, now Pat. No. 8,805,042, which is a continuation of application No. 10/598,764, filed on Sep. 11, 2006, now Pat. No. 8,014,575, application No. 13/848,638, filed on Mar. 21, 2013, which is a continuation-in-part of application No. 13/136,165, filed on Jul. 25, 2011, now Pat. No. 8,457,377, which is a continuation of application No. 10/598,764, filed on Sep. 11, 2006, now Pat. No. 8,014,575, which is a continuation-in-part of application No. PCT/US2005/008311, filed on Mar. 11, 2005.

(60) Provisional application No. 60/552,332, filed on Mar. 11, 2004.

(51) Int. Cl.
*G06K 9/00* (2006.01)
*G06T 7/00* (2006.01)
*B60R 25/00* (2013.01)
*A61B 5/00* (2006.01)
*H04L 12/40* (2006.01)

(52) U.S. Cl.
CPC ............. *G06T 7/0012* (2013.01); *A61B 5/0033* (2013.01); *B60R 25/00* (2013.01); *G06T 7/0081* (2013.01); *G06K 2209/055* (2013.01); *G06T 2207/10016* (2013.01); *G06T 2207/10072* (2013.01); *G06T 2207/10088* (2013.01); *G06T 2207/20101* (2013.01); *G06T 2207/20221* (2013.01); *G06T 2207/30012* (2013.01); *G06T 2207/30016* (2013.01); *H04L 2012/40273* (2013.01); *Y10T 428/24* (2015.01); *Y10T 428/24744* (2015.01)

(58) Field of Classification Search
None
See application file for complete search history.

(56) References Cited

U.S. PATENT DOCUMENTS

| 2003/0086596 A1* | 5/2003 | Hipp et al. | 382/128 |
| 2006/0241368 A1* | 10/2006 | Fichtinger et al. | 600/407 |
| 2010/0086185 A1* | 4/2010 | Weiss | 382/131 |

OTHER PUBLICATIONS

Long et al. ("Landmarking and feature localization in spine x-rays", J. Electron. Imaging, vol. 10, Issue 4, pp. 939-956, Oct. 2001), hereby referred to as Long.*

(Continued)

*Primary Examiner* — Tahmina Ansari
(74) *Attorney, Agent, or Firm* — Workman Nydegger

(57) ABSTRACT

Image processing, creation and analysis techniques include using computer technology to identify a plurality of structures of interest in an image, such as spinal discs in a medical diagnostic image. Such techniques can also be used to improve image creation through the use of localizers which can help identify portions of an image, and the use of computer programs to combine multiple images into a single image for review.

33 Claims, 39 Drawing Sheets

(56) References Cited

OTHER PUBLICATIONS

Kang et al. ("A new accurate and precise 3-D segmentation method for skeletal structures in volumetric CT data", IEEE Transactions on Medical Imaging, vol. 22, No. 5, May 2003, pp. 586-598), hereby referred to as "Kang".*

Archip et al. ("A knowledge-based approach to automatic detection of the spinal cord in CT images", IEEE Transactions on Medical Imaging, vol. 21, No. 12, Dec. 2002), hereby referred to as "Archip".*

\* cited by examiner

| Distance | (+) | (−) |
|---|---|---|
| 0 | | |
| 1/2 | o ○ o | o    o |
| 1 | o | o |
| 1 1/2 | oo | oo |
| 2 | oo | oo |
| 2 1/2 | ooo | ooo |
| 3 | ooo | ooo |
| 4 | oooo | oooo |
| 5 | o | o |
| (Space Above Skin) | | |
| 6 | 8 | 8 |
| 7 | 8o | o8 |
| 8 | 8oo | oo8 |
| 9 | 8ooo | ooo8 |
| 10 | oo | oo |
| 11 | 8 | 8 |
| 12 | 88 | 88 |
| 13 | 88o | o88 |
| 14 | 88oo | oo88 |
| ⋮ | | |
| 24 | 8888 | 8888 |

FIG. 15B

AXIAL SECTION OR REFORMATION
y= 2cm superior to 0,0 (center of 10 cm$^2$ grid)

SAGITTAL SECTION OR REFORMATION
x= 3cm leftward of 0,0 (center of 10 cm$^2$ grid)

IDEAL T2 FSE caudate head
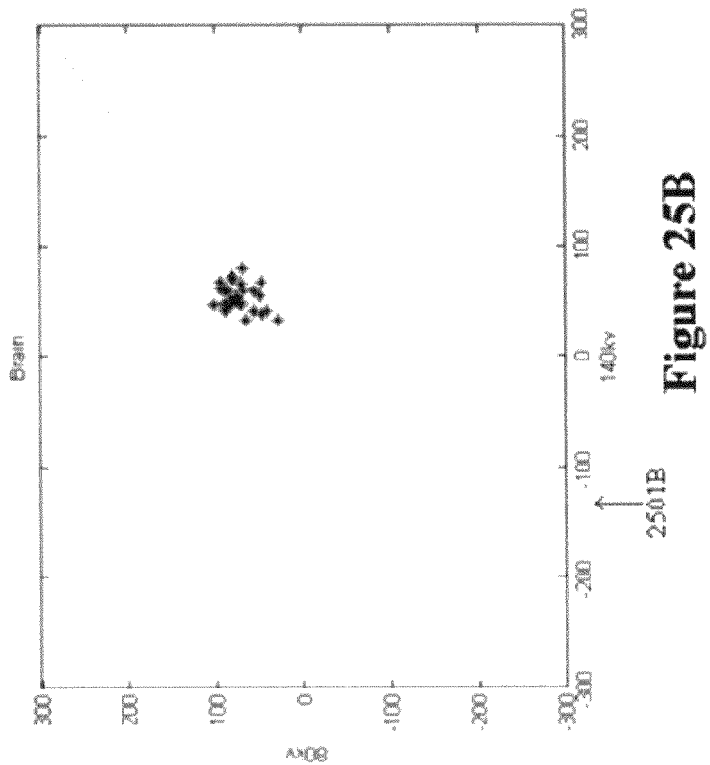
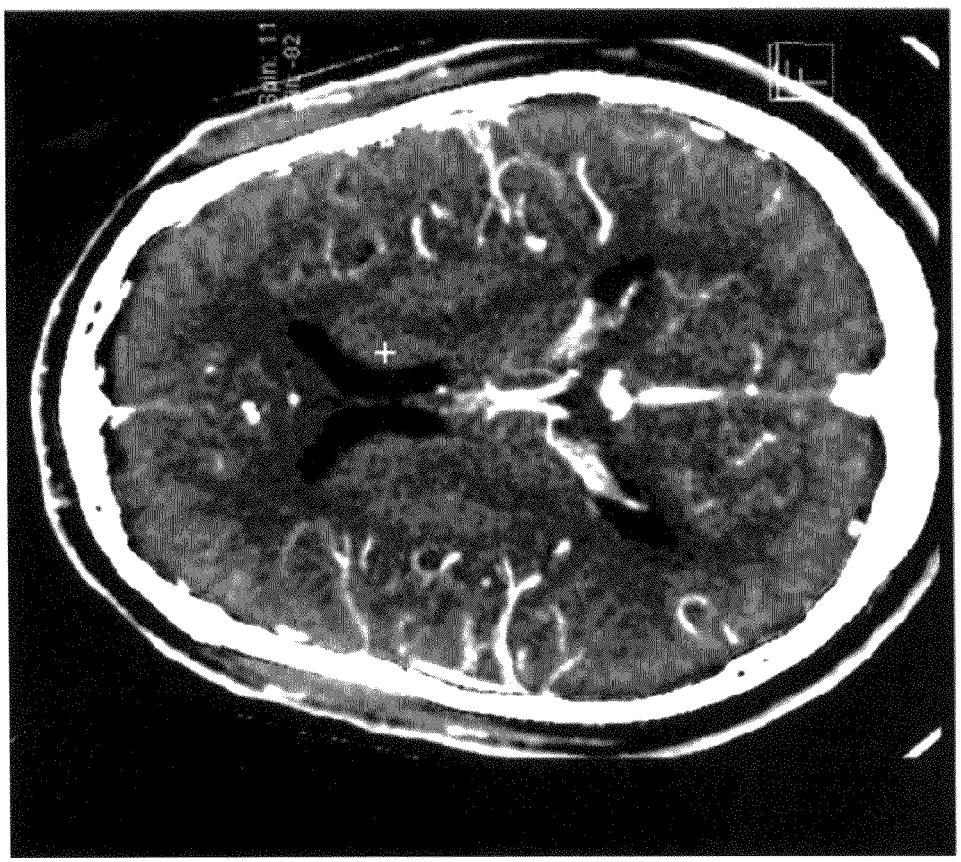
Figure 25B

SSS (iodine)
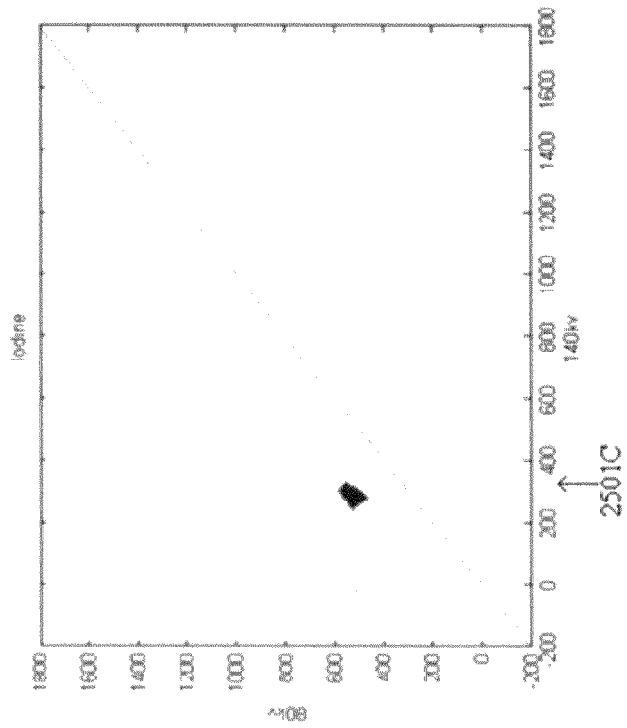
Figure 25C

COMPUTER APPARATUS FOR IMAGE CREATION AND ANALYSIS

CROSS-REFERENCE TO RELATED APPLICATIONS

This application is a continuation of U.S. application Ser. No. 12/155,803 filed Jun. 10, 2008, which was a continuation of U.S. application Ser. No. 10/598,764 filed Sep. 11, 2006 now U.S. Pat. No. 8,014,575 issued Sep. 6, 2011. This application is also a continuation in part of U.S. application Ser. No. 13/136,165 filed Jul. 25, 2011 which was a continuation of Ser. No. 10/598,764 filed Sep. 11, 2006 now U.S. Pat. No. 8,014,575 issued Sep. 6, 2011, which was a continuation in part of United States PCT application PCT/US05/08311 filed Mar. 11, 2005, which claimed the benefit of U.S. Provisional application 60/552,332 filed Mar. 11, 2004, all of which are hereby incorporated herein by reference in their entirety.

BACKGROUND

Background and Relevant Art

The disclosure of this application relates, in general, to techniques by which images can be created, analyzed and presented to health care professionals or other individuals or systems.

Image analysis can often be an exacting and difficult process. Further, as technology has progressed, image analysis has become more pervasive in a substantial variety of fields. Accordingly, it can be beneficial to utilize techniques which automate some aspects of image processing, and reduce the number of images to be examined, and/or can make the images to be examined easier to analyze.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 14A depicts a frontal view of the point localizer affixed to fabric; FIG. 14B depicts a reverse side of the point localizer of FIG. 14A; FIG. 14C is a perspective view of the point localizer and underlying fabric affixed to the skin; FIG. 14D is an enface view of the fabric with corresponding marking affixed to the skin; FIG. 14E is an enface view of the localizer affixed to skin; FIG. 14F is a diagram view of a port integrated into a tubular ring; FIG. 14G is a frontal view of a modified ring shaped localizer affixed to fabric with additional markings; FIG. 14H is a frontal view of the fabric in FIG. 14G with the localizer removed; FIG. 14I is a frontal view of a multilocalizer sheet demonstrating the adhesive backing and overlying fabric with localizers removed.

FIGS. 15A-15F illustrate a cross-shaped grid configuration; FIG. 15A is an enface view of the grid with modified square as the central hub and uniquely positioned rows of tubing radiating along the vertical and horizontal axes; FIG. 15B is a schematic of axial cross sections acquired at representative distances from the horizontal axis; FIG. 15C demonstrates the underlying marked fabric with the superimposed tubing in FIG. 15A removed; FIG. 15D is a variant of FIG. 15A with modified ring serving as a central hub; FIG. 15E depicts a limb fixation ring and angulation adjuster; and FIG. 15F depicts a radiopaque grid with underlying ruled fabric strips removed.

FIGS. 25A-25F depict how scatter plots can be used to present information underlying composite images.

DETAILED DESCRIPTION

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

This disclosure sets forth various tools and techniques which can be used in creating, analyzing and presenting images. While this disclosure focuses on applications of the described tools and techniques in the field of medicine, it should be understood that the subject matter of this application is not limited to disclosure in the medical field, could be applied in other areas as well, such as luggage screening, and bomb detection. Accordingly, the disclosure set forth herein should not be treated as implying limitations on any claims which are included in this application, or in any application claiming the benefit of this application. Instead, all terms in all claims included in this application or other applications claiming the benefit of this application should be understood as having their broadest reasonable meaning as indicated by a general purpose dictionary One technique for automated processing of images is to use an algorithm operable to automatically identify and label aspects of a medical diagnostic image (e.g., numbering vertebral discs). A labeled medical diagnostic image could then be either presented to a doctor to examine for the purpose of determining further treatments or diagnoses, could be presented to further automated systems for their internal use (e.g., autoprescription systems), or both. An example of a system which could be used for such automated processing of a medical diagnostic image is depicted in FIG. 1.

Figure 1:
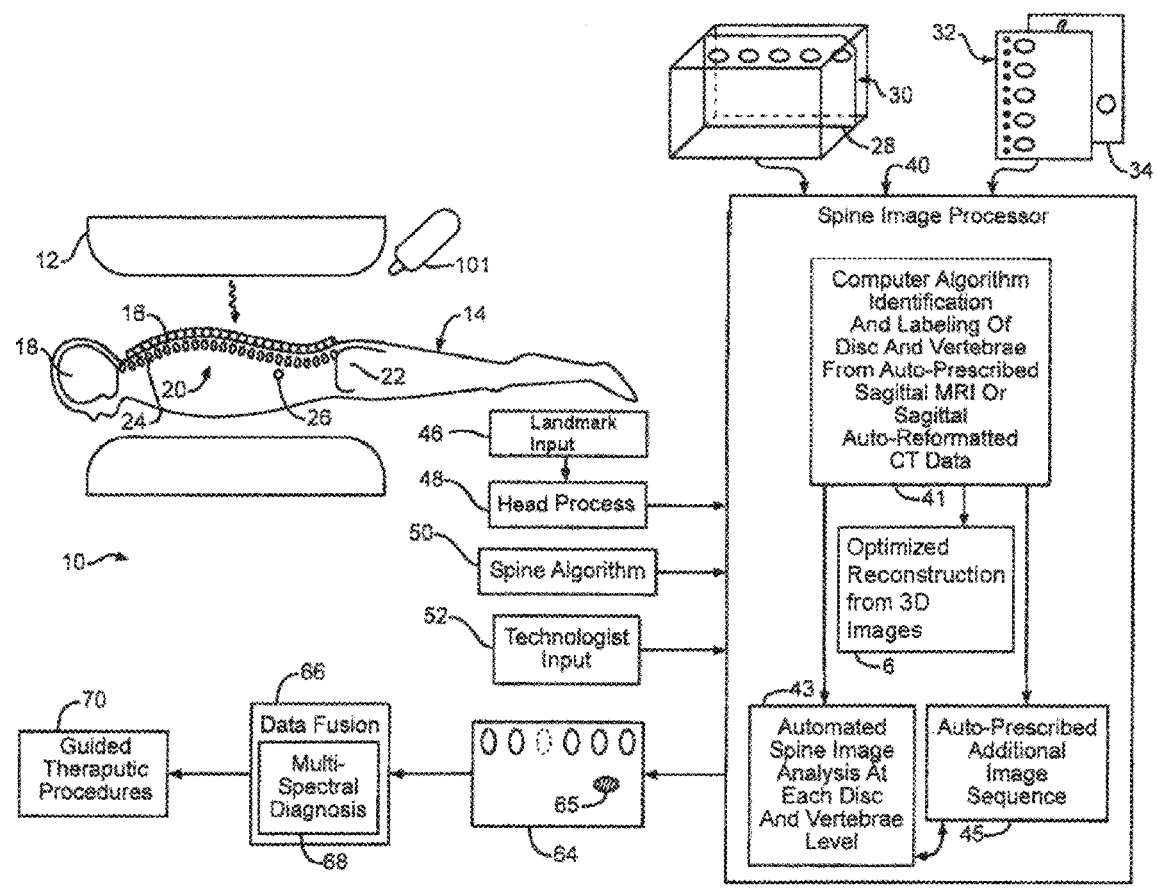
FIG. 1 is a diagram of an automated spinal diagnostic system.

FIG. 1 depicts an automated spinal diagnostic system 10. The system depicted in FIG. 1 includes a diagnostic imaging system 12, which is a system such as a magnetic resonance imaging system (MRI), or a computed tomography (CT) scanner that is capable of producing a representation of a portion (it should be understood that, in the context of this paper, a portion could be the entire patient) of a patient or other subject matter under study. Such a representation might be used to create an image which can be examined by a physician or technologist, such as a digital image displayed on a screen or a physical image printed on film, or it might be stored internally in a computer's memory and used to automate or partially automate the treatment of a patient. For the purpose of clarity, when terms such as "imaging system" and "diagnostic image" are used in this paper, it should be understood that those terms are not intended to be limited externally visible images (e.g., an image on film) and systems which produce them, but are instead intended to encompass systems which produce representations which are used in a computer's internal processes and which are not necessarily displayed to a physician or technologist. Similarly, when the term "label" is used in this paper, it should be understood to refer not only to a visible label, but to any signifier which can be used for unique and consistent identification.

In FIG. 1, the diagnostic imaging system 12 is used to image a torso of a patient 14. As depicted in FIG. 1, the torso of a patient 14 is advantageously covered by a skin/surface marking system 16, such as described in U.S. patent application Ser. No. 10/598,764, "AUTOMATED NEUROAXIS (BRAIN AND SPINE) IMAGING WITH ITERATIVE SCAN PRESCRIPTIONS, ANALYSIS, RECONSTRUCTIONS, LABELING, SURFACE LOCALIZATION AND GUIDED INTERVENTION," the disclosure of which is hereby incorporated by reference in its entirety. In some embodiments, the skin/surface marking system 16 might serve as an integrated multimodality, multi-functional spatial reference. That is, the skin/surface marking system 16 might be designed in such a way as to be visible in medical diagnostic images produced by different imaging modalities (e.g., CT scan, MRI system), and might also be designed in such as a way as to achieve multiple functions (e.g., to produce a visible representation in the medical diagnostic image and to leave a marking on the patient's skin or some other surface). In an embodiment following the diagram of FIG. 1, the diagnostic imaging system 12 might produce one or more medical diagnostic images depicting the patient's skull 18, the patient's full spine 20, and/or the patient's pelvic bones 22. In some embodiments, the diagnostic imaging system serves to perform an automated MRI technique that rapidly surveys the entire spine, labeling all discs (flattened anatomical structures which lie between adjacent vertebrae in the spine) and vertebrae (the bones or cartilaginous segments forming the spinal column). C-T-L vertebrae and discs can be readily identified and definitively numbered by visual inspection or semi-automated computer algorithm ("ASSIST").

Correctly identifying each spinal structure, that is, each vertebra or disc, in the spine 20 is complicated in certain instances when the skull 18 and/or the pelvic bones 22 are not imaged. In some instances, a vertebra or disc (depending on whether CT, MRI, or some other imaging modality, is being used) will fail to image properly, depicted at 24. In addition, the highly predominant number of twenty-four mobile pre-sacral vertebrae may not be the case for certain individuals. Having the correct vertebrae references may be important in localizing a suspicious lesion 26, which might be later targeted by some type of therapeutic instrument, that is any tool or device which can be used to help improve or restore health. A non-limiting example of such a therapeutic instrument is the radiation device 101 depicted in FIG. 1. Approaches to addressing the difficulties posed by correct identification of spinal structures are set forth herein.

As shown in FIG. 1, the diagnostic imaging system 12 may derive a sagittal image 28, that is, an image of a plane parallel to the median plane of the body, of the torso of the patient 14 from a volume CT scan 30 (also called a sagittal section). Alternatively, the diagnostic imaging system 12 may produce an upper cervical-thoracic sagittal image 32 and a lower thoracic-lumbar sagittal image 34, such as from MRI. In this application, a thoracic lumbar sagittal image should be understood to mean a sagittal image which includes a representation of the bottom (inferior) portion of the spine, while the term cervical thoracic sagittal image should be understood to mean a sagittal image which includes a representation of the top (superior) portion of the spine. In some embodiments following the diagram of FIG. 1, a spine image processor 40, which may be a process hosted by the diagnostic imaging system 12 or by a remote device, performs a number of subprocesses to correctly identify and label the spine 20.

Several approaches to implementing systems which are operable to obtain and label medical diagnostic images of patients have been found to be effective. For example, in one instance, MRI studies were performed on a clinical 1.5 T magnet with standard 4-channel quadrature array 6-element spine coil and surface coil correction algorithm. Contiguous two-station 35 centimeter (cm) field of view (FOV) sagittal fast gradient-recalled echo (FGRE) sequences were pre-programmed, providing full cervical, thoracic and lumbar (C-T-L) spine coverage. Combined sagittal FOV of 70 cm., 7 sections, scans from 15 millimeters left of midline to 15 millimeters right of midline (L15-R15), 4 millimeter (mm) section thickness with 1 mm intersection gap; 512×352 matrix, 1 excitation/image acquisition (nex), repetition time (in milliseconds) (TR) 58, echo time (in milliseconds) (TE) 2.0, 30° flip, Bandwidth (BW) 15.6 kHz; 21 sec×2 stations=42 sec. To facilitate and standardize auto-prescriptions, a line was drawn on the spine coil for the technologists to landmark (set as scanner's 0 coordinate) rather than have the technologist use a superficial anatomic feature. The coil has a contoured head/neck rest assuring grossly similar positioning of the cranial-cervical junction of each patient relative to this landmark. The spine image processor 40 was implemented in MATLAB 7.

In another instance, images were prepared using out-of-phase FGRE sequencing (512×352, TR 57-62 msec, TE 2.2 msec at 1.5 T and TE 1.4 msec or 3.2 msec at 3.0 T) and experimental FSE IDEAL sequencing, the latter with T1 and/or T2 weighting. In this instance, for T1 weighting, TR ranged from 350-750 msec, TE 14-33 msec, ET 1-4, frequency encoding 320-512 and phase encoding 224-256. For T-2 weighting, TR ranged from 1867-2600 msec, TE 20-70 msec, ET 8-10, frequency 320-512 and phase 224-352. On different types of hardware, 7, 9 or 11 sections were obtained in a single acquisition. Acquisition time for FGRE sequences was 21-22 seconds to accommodate breath holding, and IDEAL sequencing was limited to less than five minutes. In this instance, the spine image processor 40 was configured to accommodate variable number of sections; integrate age, gender and weight information available in DICOM header with a database to constrain search; compare candidate disc properties with estimated values derived from the database; use a search algorithm constraining subsequent discs based on previous (more cephalad) disc characteristics; and review intensity statistics of candidate discs. Of course, it should be understood that other approaches are also possible, and that the approaches set forth herein are intended to be illustrative only, and not limiting.

Returning to the discussion of FIG. 1, in block 41, a computer algorithm is hosted on the spine image processor for the identification and labeling of disc and vertebrae from auto-prescribed sagittal MRI or sagittal auto-reformatted CT data, described in greater detail below. This information may be advantageously provided to an automated spine image analysis algorithm 43 that further characterizes each disc and/or vertebrae level. Alternatively or in addition, this information from block 41 may be advantageously provided to an auto-prescription algorithm 45 for additional image sequences, utilizing the identified spinal landmarks as references. Further, the additional processes 43, 45 may exchange information with each other, such as detailed analysis and diagnosis of a particular vertebra in block 43 being enabled by auto-prescribed detailed images in block 45.

In an illustrative implementation of techniques for labeling spinal structures in a medical diagnostic image, an algorithm keyed on a unique definable reference landmark for characterization and unambiguous labeling of spinal structures in the image. An example of such keying which might be used with a MRI medical diagnostic image is to use the centroid of the top (most cephalad) intervertebral disc (C2-3) as a key landmark. Alternatively, the top vertebrae (C1 or C2), or other unique identifiable structure, or other landmark may be employed.

Figure 9:
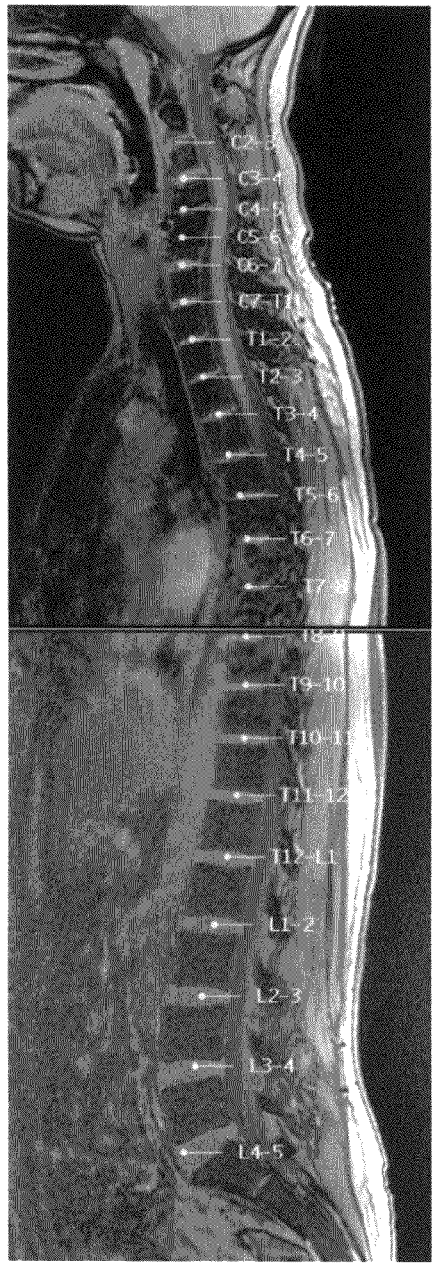
FIG. 9 is a sagittal image through the entire spine of a patient with 23 mobile/presacral vertebrae with correct auto-labeling of first 22 interspaces.
Figure 10:
FIG. 10 is a sagittal image through the entire spine of a patient with 25 potentially mobile presacral vertebrae with correct auto-labeling of the first 23 interspaces.

In FIG. 1, in block 46, the top intervertebral disc is identified, which may be automated in block 48 by interfacing with an automated cranium identification system, such as described in U.S. patent application Ser. No. 10/803,700, "AUTOMATED BRAIN MRI AND CT PRESCRIPTIONS IN TALAIRACH SPACE" to Dr. Weiss, filed 18 Mar. 2004, the disclosure of which is hereby incorporated by reference in its entirety. Alternatively, logic may be incorporated into the spine image processor 40 wherein a spine algorithm in block 50 recognizes a top vertebra or intervertebral disc. As a further alternative and as fall back option should automated means fail, in block 52 a technologist input is received to identify the top vertebra or intervertebral disc. During testing, the neuroradiologist could readily visualize and definitively number all cervical-thoracic-lumbar (C-T-L) levels on ASSIST localizers. 6/50 patients had a congenital shift in lumbar-sacral transition; 3 with 23 mobile pre-sacral vertebrae (as shown in FIG. 9) and 3 with 25 mobile pre-sacral vertebrae (as shown in FIG. 10). Based upon manual placement of a single seed in the C2-3 interspace, in the illustrative version with 50/50 cases performed by the spine image processor 40 the automated disc detection and numbering algorithm was concordant with neuroradiologist assignments in 50/50 (100%) of cases.

With a labeled disc image 64, correct relative location to other imaged tissue of interest 65 may be used for further diagnostic procedures or therapeutic intervention. For instance, data fusion (block 66) might allow images taken with the same type of imaging modality at different times to be correlated, which could facilitate monitoring growth progression of a suspicious lesion or changes due to an intervening injury. In addition, images taken with different imaging modalities might be cross referenced to perform multi-spectral diagnoses (block 68), wherein information on a type of tissue may be gained by its different responses to various types of electromagnetic spectra. With tissue diagnosis complete, in block 70 a guided therapeutic procedures algorithm may correctly orient a therapeutic agent, such as the radiation device 101 or a guided minimally invasive surgical instrument (not shown). Alternatively, for an externally oriented procedure, a surgeon may reference either the relative location to a known spinal structure (e.g., vertebrae) and/or reference the skin/surfacing marking system 16.

During testing, a first batch of 27 cases was initially run with an algorithm 100 developed using previously obtained, non surface-coil corrected ASSIST images. As the first step 102, we input cervical thoracic (top half), and thoracic lumbar (bottom half) spines. A threshold and a median spatial filter are applied to the search region. Then, additional disc constraints were applied to identify longest chain in top and bottom images. Candidate discs must extend onto at least two adjacent slices. As used in this application, adjacent slices should be understood to refer to two slices for which the space between those slices is not represented in a medical diagnostic image. Objects at the boundary or touching the boundary of the search region were excluded. Different threshold values and candidate discs' constraints are applied to the top, and bottom half image.

Figure 2:
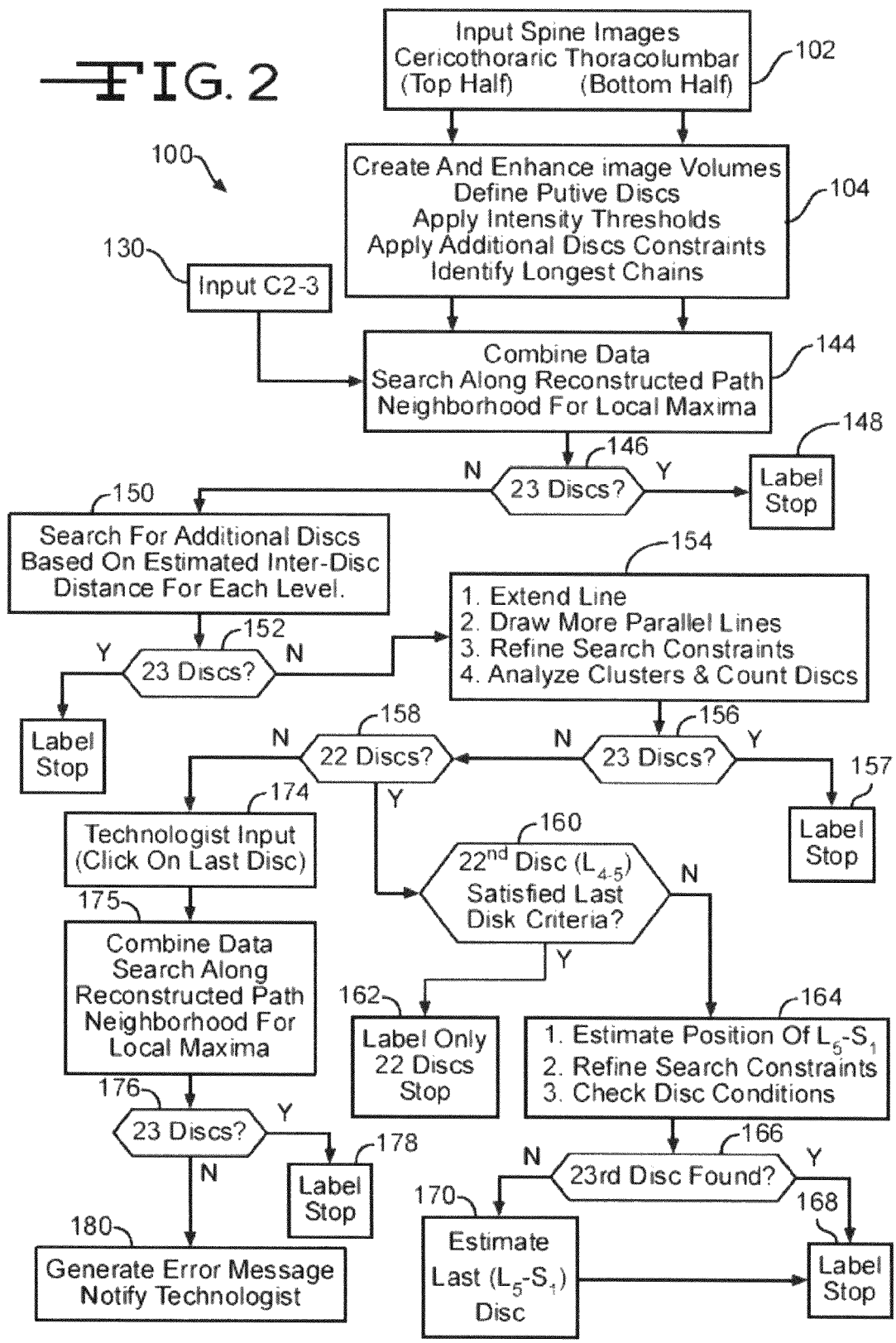
FIG. 2 is a flow diagram of a spine identification sequence of operations or procedure for the automated spinal diagnostic system of FIG. 1.

In FIG. 2, the automated disc detection and numbering algorithm 100 is a multi-step iterative process. DICOM (i.e., Digital Imaging and Communications in Medicine) ASSIST images of the cervical thoracic (top half), and thoracic lumbar (bottom half) spine are first input into MATLAB 7 (The Math Works, Inc., Natick, Mass.) for digital image processing (block 102). In the illustrative example, the digital image processing is based on analysis of voxels, or units of graphic information. In the illustrative example, because each medical diagnostic image represented a sagittal slice, the voxels represent locations in three dimensional space, though other embodiments might alternatively be based on analysis of locations in two dimensional space, or on other units of information.

Initially, the two data sets (top and bottom half) are processed to obtain putative discs separately, utilizing different threshold values and disc constraint parameters (block 104). This results in upper and lower images (106, 108), such as depicted in, respectively, FIGS. 5 and 6. As used in this application, a disc constraint should be understood to mean a criteria applied to determine whether a structure represented by a plurality of voxels is a spinal disc. Similarly, a spinal structure constraint should be understood to mean a criteria applied to determine whether a structure represented by a plurality of voxels is a spinal structure. The images 106, 108 are enhanced with a tophat filter and background noise is suppressed. A posterior edge 110 of the back is then identified in each image 106, 108 and search regions 112, 114 assigned respectively. The algorithm 100 thresholds and applies a median spatial filter to the search regions. Voxels 116 exceeding threshold values are then subjected to additional constraints.

There are a variety of approaches to the application of these constraints to the voxels. In some implementations, voxels can be subjected to constraints which are appropriate for normal spinal morphologies (e.g., default constraints), which may or may not be preprogrammed for the algorithm. Thus, in some cases, an algorithm can be designed so that acceptable voxels are selected to extend onto at least two adjacent sagittal sections but not touch the boundary of the search region 112, 114. Similarly, such an algorithm might include a requirement that the acceptable voxels must lie 6-80 mm in the cervical thoracic (C-T), and 8-100 mm in the thoracic lumbar (T-L) region from adjacent acceptable voxels. Of course, other approaches are also possible. For example, in some cases, an algorithm might be configured to utilize a database of medical diagnostic images which can be used to derive constraints in a way which is specific to an image under study. In such an approach, where a database is utilized to customize the search for acceptable voxels, an algorithm such as described herein could be augmented through machine learning. That is, as more images are received and processed, those images could be included in the database, so that more fine grained and accurate customizations could be made based on the increasing data set.

Figure 3:
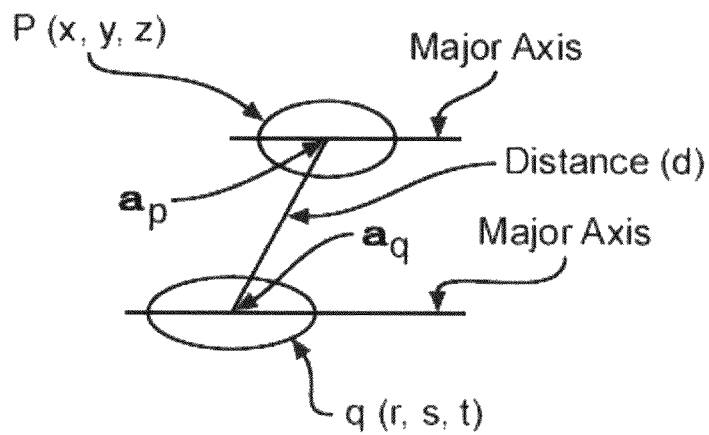
FIG. 3 is a diagram of a projection function of adjacent objects; $a_p$ and $a_q$ represent the angles between the line connecting candidate disc p and q through their centroid and the major axis of discs p and q respectively, wherein $0 < a_p < 90°$; let $d_c$ be the value of d for any candidate disc in cervical-thoracic spine region and $d_L$ in the thoracic-lumbar spine, then 6 mm$<d_c<$80 mm and 8 mm$<d_L<$100 mm.
Figure 4:
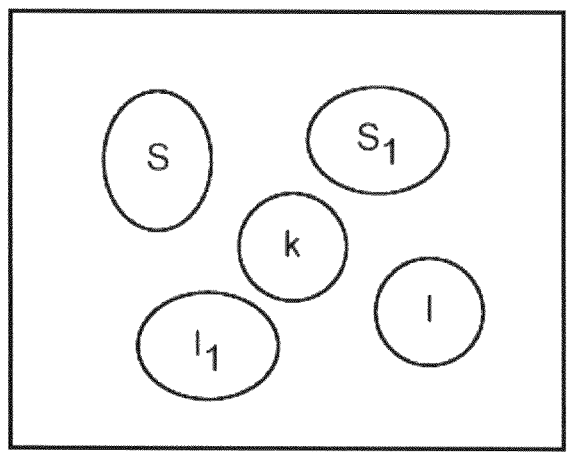
FIG. 4 is a diagram of distance constraint chains with a cluster, k, is part of a disc chain if its closest superior neighbor has k as its closest inferior neighbor and k's closest inferior neighbor has (k) as its closest superior neighbor.
Figure 5:
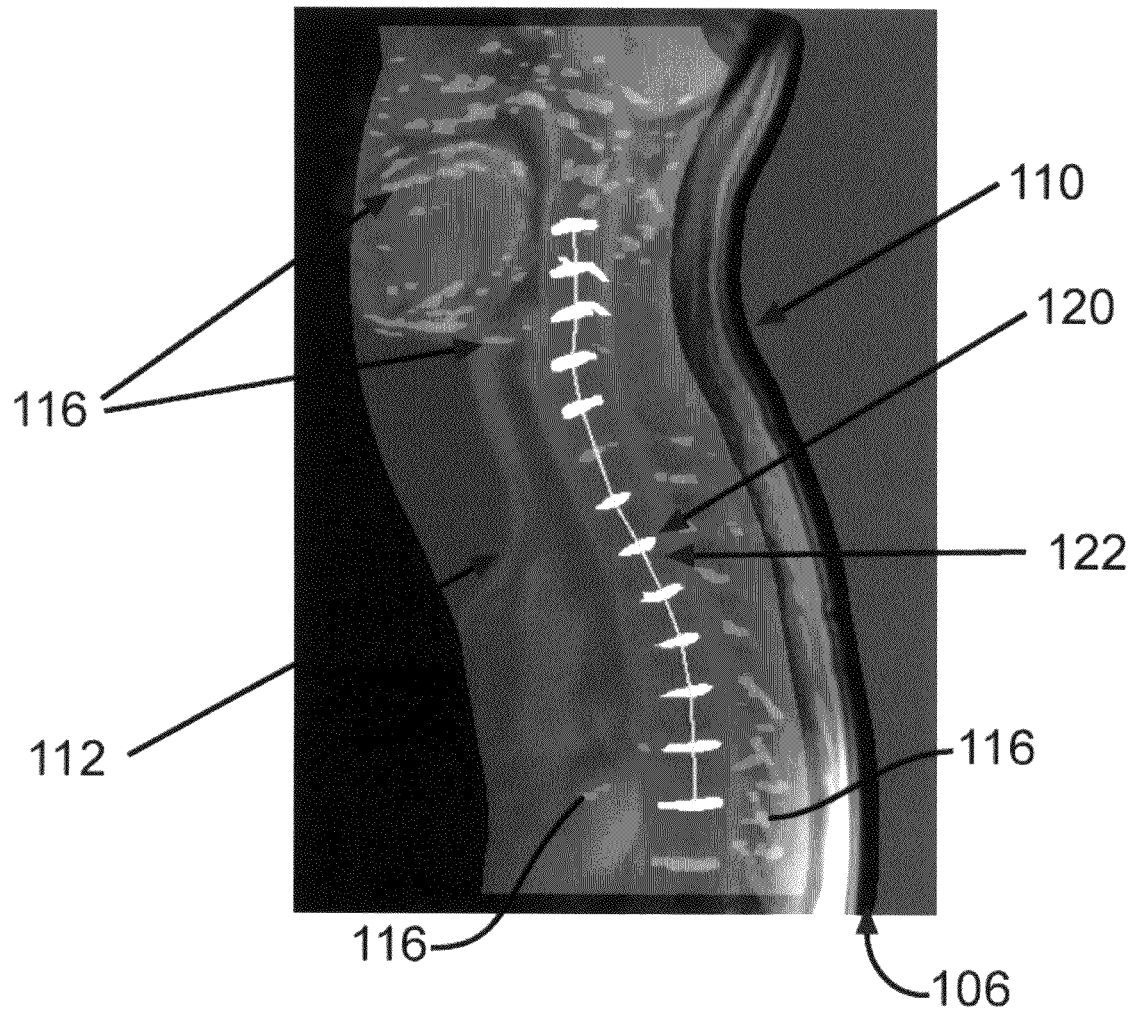
FIG. 5 is a 7-slice sagittal MRI projected image volume having a 35 cm FOV top half illustrating a search region where voxels exceeding an intensity threshold are depicted with those meeting additional disc constraints highlighted as putative discs and connected by a curved line through their centroids.
Figure 6:
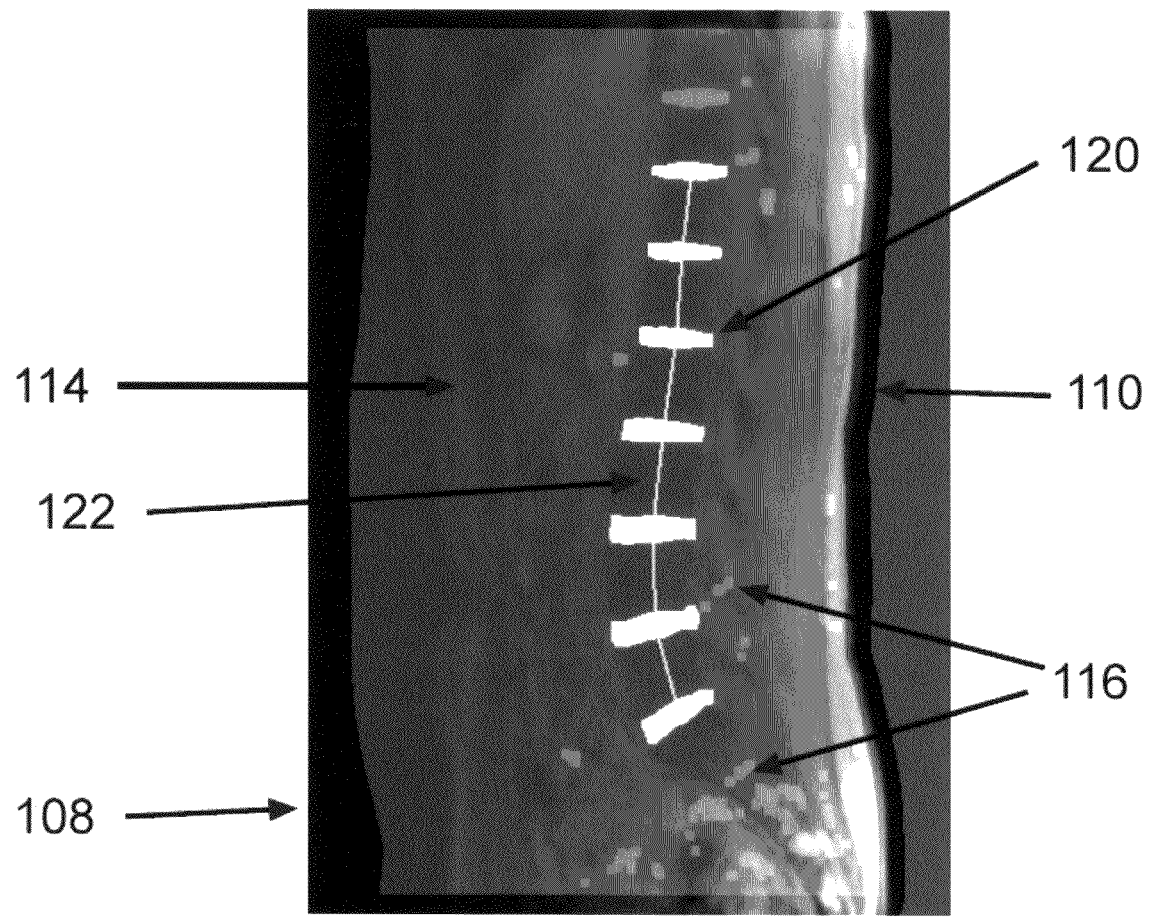
FIG. 6 is a 7-slice sagittal MRI projected image volume having a 35 cm FOV bottom half illustrating a typical search region wherein voxels exceeding intensity threshold are depicted with those meeting additional disc constraints highlighted as putative discs and connected by a curved line through their centroids.

Continuing with the discussion of how images can be processed, in some implementations, after the acceptable voxels are identified, the algorithm can continue with identification of centroids of candidate discs. These centroids, that is, voxels with coordinates determined by a weighted mean of the coordinates of the voxels in a voxel cluster, the weight of the coordinates being determined by an attribute such as intensity of the voxel at that coordinate, of these acceptable voxel clusters 120 (candidate discs) are then connected by curved line 122. Additionally, the identification of centroids can be facilitated by considering the possible relationships between discs. For example, in some cases the algorithm might assume that the angle subtended by the line 122 connecting the centroid of adjacent candidate discs 120 and the major axis of these discs will be between 450 and 1350 in both the C-T and T-L spine. Similarly, in some cases where a database of medical images is used to modify processing, the algorithm might consider the relationship between candidate discs in archival images in the database which have attributes which are similar to those of the image under study (e.g., if the image under study is from a patient with scoliosis, then scoliotic images from the database can be used to determine the relationship between adjacent discs for purposes of identifying candidates). In FIG. 3, projection analysis is used to constrain disc assignments. Furthermore, for a disc (k) to be considered part of a chain, its closest superior neighbor must have k as its closest inferior neighbor and k's closest inferior neighbor must have k as its closest superior neighbor. In FIG. 4, an angle relative to the major axis is evaluated to constrain disc assignments. The algorithm selects the longest disc chain in the C-T and T-L regions respectively (FIGS. 5, 6).

Figure 7:
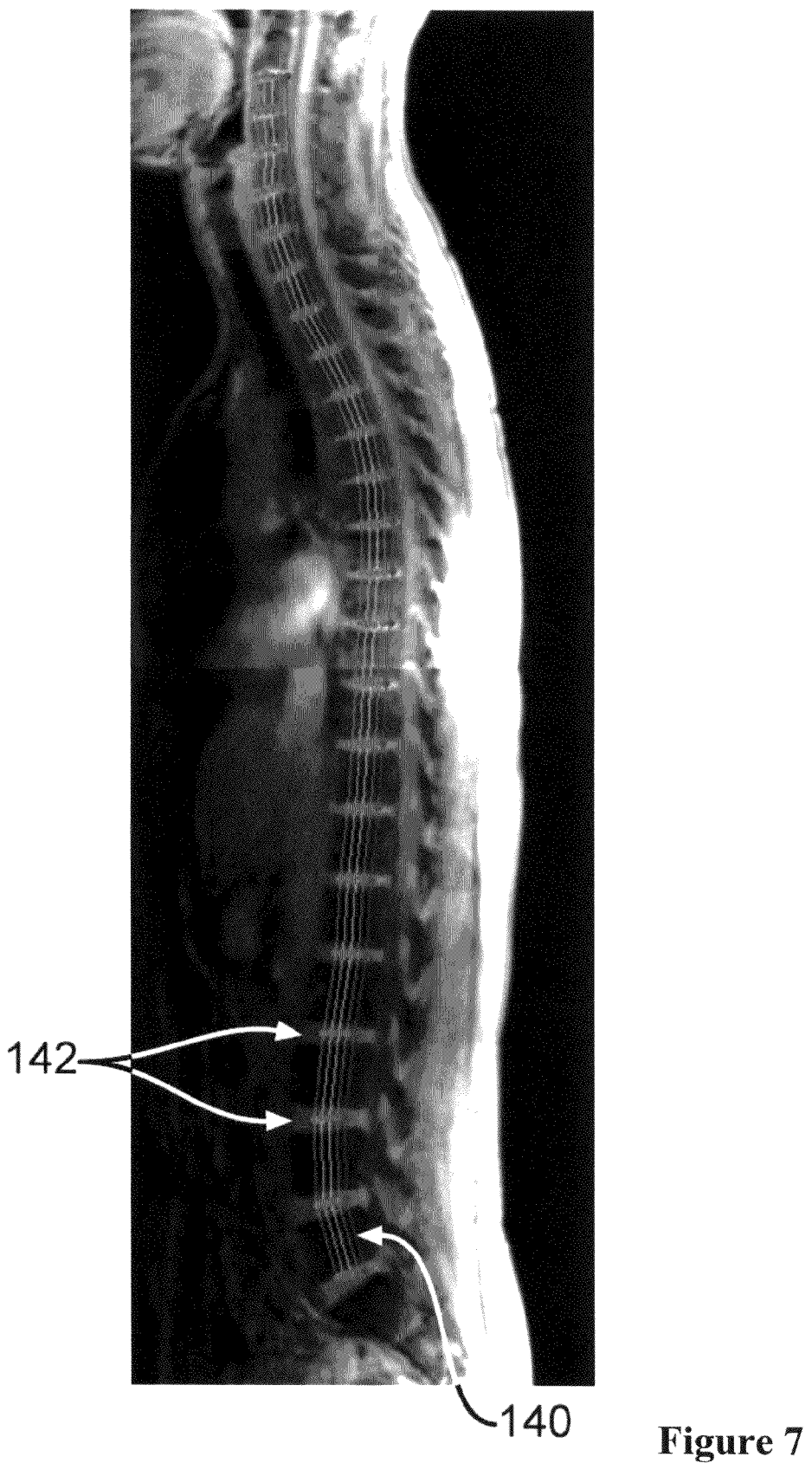
FIG. 7 is a combined sagittal image depicting search paths parallel to the curved line of FIG. 6 connecting a centroid of a C2-3 disc with longest disc chains from top and bottom half images (FIGS. 5 and 6). Dots correspond to local maxima along these paths.
Figure 8:
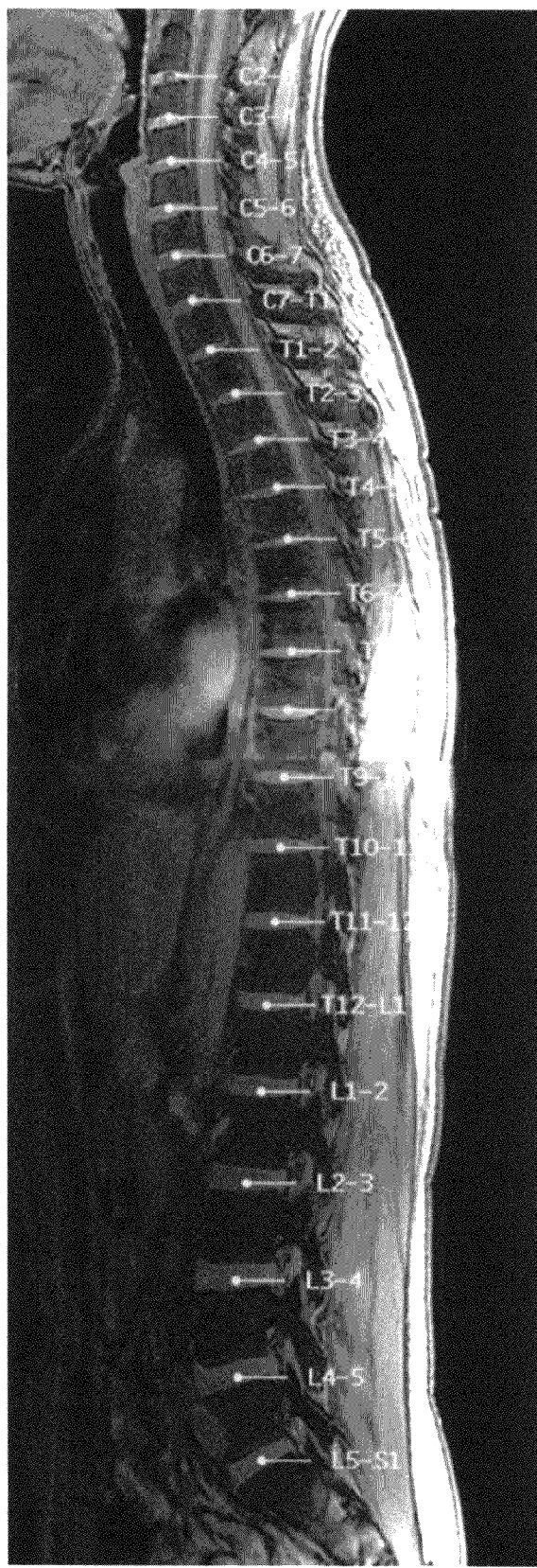
FIG. 8 is a sagittal image through the entire spine with all intervertebral discs auto-labeled with labeling of vertebrae omitted for clarity with three-dimensional (3-D) coordinates generated by an algorithm providing a means for discs or vertebral bodies to be labeled in any subsequent imaging plane providing no gross inter-scan patient movement.

Continuing with the illustrative algorithm depicted in FIG. 2, in block 130, the technologist is instructed to approximate (click on) the centroid of C2-3 at any time during or before the aforementioned candidate disc evaluation. The centroid of C2-3 and the longest disc chains in the C-T and T-L spines are connected with a straight line. Using 3D linear interpolation, the program searches along this line and twelve adjacent parallel lines 140, represented by only four in FIG. 7 for clarity due to their superimposition in the sagittal projection. After applying Gaussian filters, the algorithm 100 finds local intensity maxima along each path (equivalently, the algorithm might also search for other extrema, such as local intensity minima, depending on the imaging modality and image data obtained). Points 142 that are less than 7.5 mm apart are grouped into clusters. These clusters are analyzed based on orientation, eccentricity, and spatial relationship relative to other clusters (block 144 of FIG. 2). Then, if twenty-three (23) discs are selected in block 146, the computer auto-labels these discs or adjacent vertebrae and stops (block 148). The process of labeling discs or vertebrae might result in the production of images as depicted in FIGS. 8-10.

In the illustrative algorithm, if 23 discs are not selected in block 146, search criteria and thresholds can be refined. There are a variety of methods by which such refinement can take place. For example, in some implementations, the following formula for inter-disc height for each level can be used for the refinement (Equation 1):

$$h=0.6(M) \text{ for } L=1,2, \text{ or } 3 \text{ else}$$

$$h=M+(L-1.2)*0.05(M) \text{ for } L>3$$

Where h is inter-disc height, L is the disc level, and M is the distance along the line through the centroids/23 (mean). It is also possible that a database of archived medical diagnostic images such as described above could be used in which the estimated inter-disc height could be determined based on the observed inter-disc height from archival images which have attributes which are similar to the attributes of the image under study (e.g., patients having a similar height).

Continuing with the illustrative algorithm depicted in FIG. 2, if, in block 150, 23 discs are not yet identified, the algorithm 100 extends the search line inferiorly. One technique for extension of the search line is to use a formula based on the estimated position (Ex, y) of the missing disc(s) as shown below (Equation 2):

$$E_{(x_j, y_j)} = (x_{j-1}, y_{j-1}) + h_a(x_{j-1}, y_{j-1}) \times \sum_{1}^{j-1} \frac{h_s(x, y)}{h_a(x, y)}$$

In that formula, $h_a$ is the average vertebral height from a training set of previously processed medical images, and $h_s$ is the vertebral height from the subject in question. The program searches for local maxima along this line extension and 24 adjacent parallel lines. A further determination is made in block 152 as to whether 23 discs have been found. Iteration continues as long as twenty-three (23) discs are not selected, as represented by block 154 that extends the search and the further determination of block 156, which labels the vertebrae if 23 are selected (block 157). Depending on the resources available in a particular implementation, the value ha in the equation above can be an average value taken from some set of training data, or could be a more customized value for a particular patient. As an example of how a customized value might be used, in cases where there is available a database of previously processed images, the program employing the algorithm of FIG. 2 could request that the database provide an average value for vertebral height for patients having characteristics similar to the patient under study (e.g., height within two standard deviations of the height of the patient), or could request that the database retrieve such images, and then the program would calculate the average vertebral height value directly.

If not 23 discs in block 156, then in block 158 a further determination is made that twenty-two (22) discs are selected. If so, the algorithm 100 will determine in block 160 whether the last identified level (L4-5) satisfies criteria for the terminal pre-sacral interspace suggesting a congenital variant with 23 rather than the typical 24 mobile presacral vertebrae. In some implementations, to be considered a terminal disc, the centroid of the 22nd disc must lie within 25% of its expected location E(x, y) relative to the 21st disc. Additionally, an algorithm can be implemented such that the centroid must lie posterior to the centroid of the 21st disc and the slope of the 22nd disc must be positive and greater than that of the 21st disc. If those criteria are met, then twenty two discs will be labeled (block 162).

If 23 discs are found in block 166, the discs are labeled in block 168. Else, if the terminal disc criteria are not met in block 166, the position of the 23rd (L5-S1) disc is estimated using Equation 2 (block 164), and search constraints refined. If the 23rd disc is still not identified in block 166, the disc is presumed to be severely degenerated or post-surgical and the estimated position for L5-S1 will be accepted in block 170 and the discs thus labeled (block 168).

If less than 22 discs are identified by the algorithm in block 158, then the algorithm depicted in FIG. 2 can be implemented such that the technologist will be instructed in block 174 to approximate (click on) the centroid of the last disc. The "combine data" step from block 144 is repeated in block 175 and if necessary the "search for additional discs" step as well. If twenty-three (23) discs are selected in block 176, then the discs are labeled in block 178. Else, if twenty three (23) discs are still not selected in block 176, the algorithm prints out, "Sony, computer unable to detect all the discs. Require technologist revision." (block 180). As a variation, in some cases, rather than requesting technologist input, the computer could extract additional information from subsequently or concurrently obtained co-registered sequences such as the separate water and fat images depicted in FIG. 20A. For example, in some cases, and algorithm could use information obtained through images obtained through the Iterative Decomposition of Water and Fat with Echo Asymmetric and Least Squares Estimation (IDEAL) approach. Such images can be used to help identify spinal structures due to the fact that different structures (e.g., discs) would have different fat and water components, even though they would be represented in a nearly indistinguishable manner in a conventional water+ lipid image. Of course, it is also possible that, in some implementations both allowing a technologist revision and utilizing the additional information provided by fat-water decomposition could be included. Accordingly, the description above should be understood as being illustrative only, and not limiting.

Figure 11:
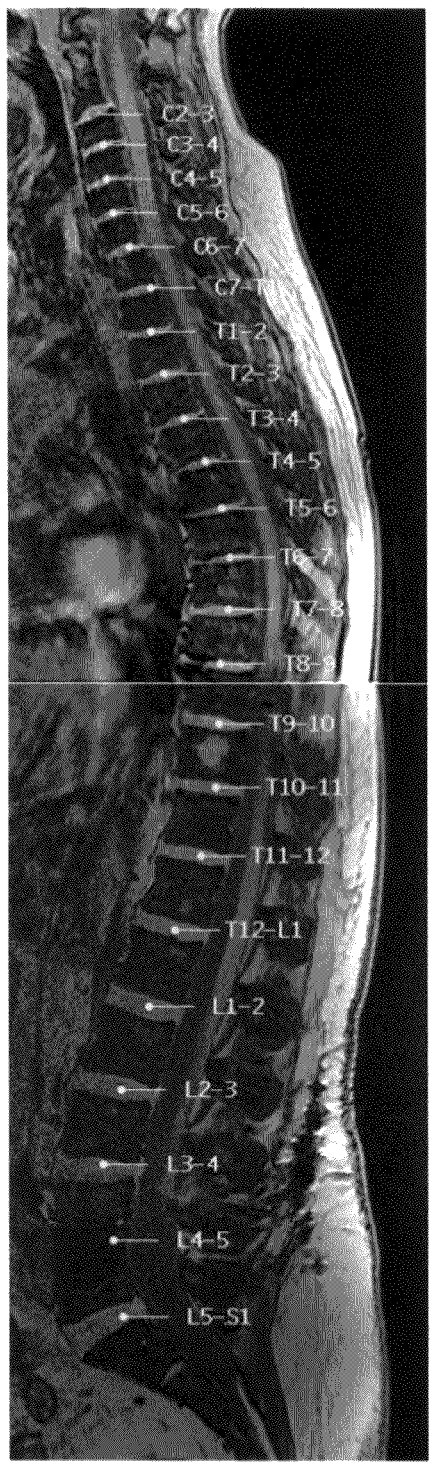
FIG. 11 is a sagittal image through the entire spine of a patient with surgically fused L4-5 interspace and associated artifact from a metallic cage with correct labeling of all 23 interspaces including a good approximation of the L4-5 disc.
Figure 12:
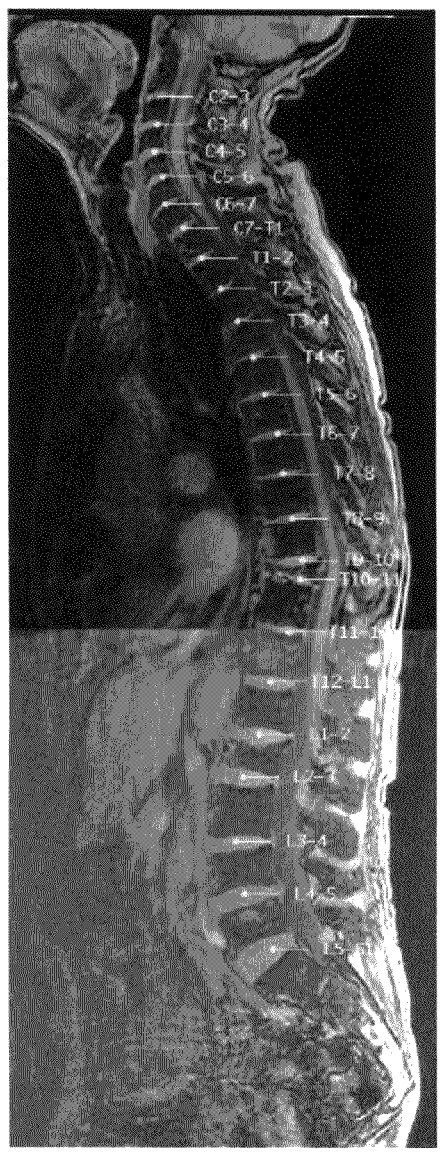
FIG. 12 is a sagittal image through the entire spine of a patient with labels generated using robust disc discrimination and Gaussian filters.

During testing, an algorithm such as described above with regard to FIG. 2 was implemented and run on an INTEL (San Jose, Calif.) personal computer with a 2.8 Ghz Xeon processor. For the test, computer auto-labeling was compared to independent neuroradiologist assignments for each patient's study. The automated spine MRI sequencing provided a robust survey of the entire C-T-L spine in 42 seconds total acquisition time. In all patients (50/50), the neuroradiologist could readily visualize and definitively number all C-T-L levels on the ASSIST localizers. These included six patients with a congenital shift in their lumbar-sacral transition; three with 23 mobile pre-sacral vertebrae (FIG. 5) and three with 25 mobile pre-sacral vertebrae (FIG. 6). Several patients had post-operative spines to include metallic instrumentation (FIG. 7). During this testing, the exemplary algorithm was accurate in all 50/50 cases (100%) of the patients to include the original 27 patients plus 23 subsequent cases, despite the presence of congenital variations (FIGS. 5, 6), post-operative changes (FIG. 11), and prominent disc or vertebral pathology (FIG. 12) in this patient population. None of the 50 cases required technologist input of more than a single interspace (C2-3) though the algorithm provides such an iterative pathway if necessary. In the vast majority of cases, the algorithm 100, running on a personal computer with a 2.8 GHz processor, took less than 2 minutes to identify and label all intervertebral discs or vertebrae.

Additional variations on an algorithm such as described above could be implemented to extend its applicability to a wider section of the population. For example, in some cases where the medical diagnostic images analyzed are sagittal sections, the algorithm could be modified so that, in scoliotic patients, additional sagittal sections could be obtained, resulting in complete spinal coverage even given the abnormal curvature of those patients' spines. Similar modifications could be made in an implementation configured to analyze three dimensional medical diagnostic images, where a larger portion of the three dimensional image could be analyzed to locate spinal structures. Also, while the illustrative disc detection algorithm 100 described above requires manual input of the most cephalad disc, C2-3, to achieve maximal accuracy, it should be appreciated that automated computer detection of this interspace may be implemented. The C2-3 disc may be readily discerned on midline sagittal head images with a 22-24 cm FOV, (as described in 2004 at pages 233-37 of volume 25 of the American Journal of Neuroradiology and in 2003 at pages 922-29 of volume 24 of the American Journal of Neuroradiology, the teachings of which are incorporated by reference) or ASSIST 35 cm FOV cervico-thoracic spine images based on several unique features. These include the characteristic shape of the C2 vertebrae and relatively constant relationship to the skull base and cervico-medullary junction. Alternatively, in some instances, such as implementations using MRI sequencing and disc detection algorithms as described herein the most cephalad disc space identified may simply be labeled C2-3.

Additionally, it is possible that, in some instances, rapid volumetric MRI and CT imaging of the bring, spine or entire body and rapid fat-water MRI decomposition techniques can be exploited to make disc detection and other algorithms more robust. For example, as the calvarium, spine and their contents are nearly symmetric bilaterally, if volumetric MRI or CT images of these structures are obtained, a plane of symmetry can be automatically derived using a cost minimization function designed to reduce differences between the right and left side of the body. Weighted functions might emphasize structures near the midline or with particular MRI or CT characteristics. Volume data reconstructed along this plane of symmetry corresponds to the patient optimized midline sagittal image. This image could then be utilized by the AC-PC searching algorithm or ASSIST algorithms previously described. Having the midline of these structures defined would also facilitate computer detection of asymmetric regions, which might signify pathologic processes and thus be worthy of further image interrogation.

Figure 23:
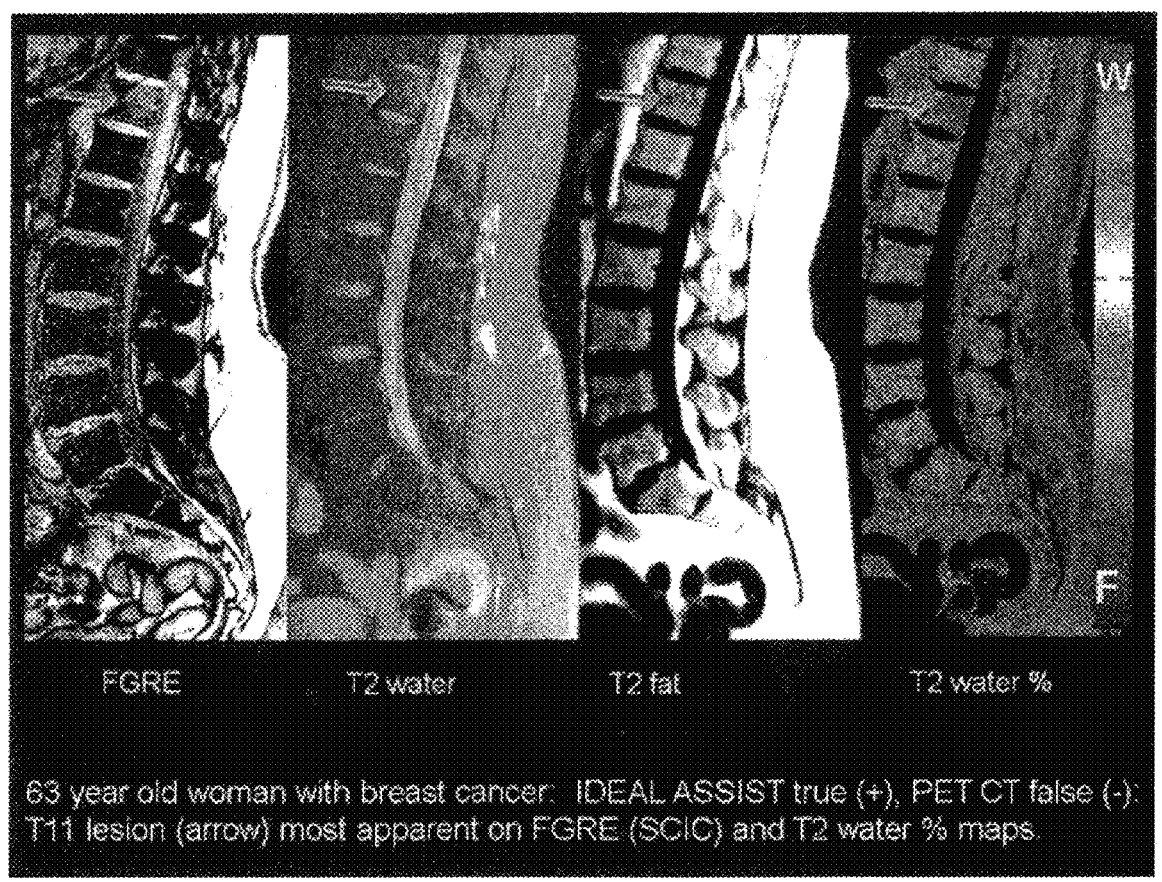
FIG. 23 depicts how IDEAL ASSIST can be utilized in a diagnostic process.
Figure 24:
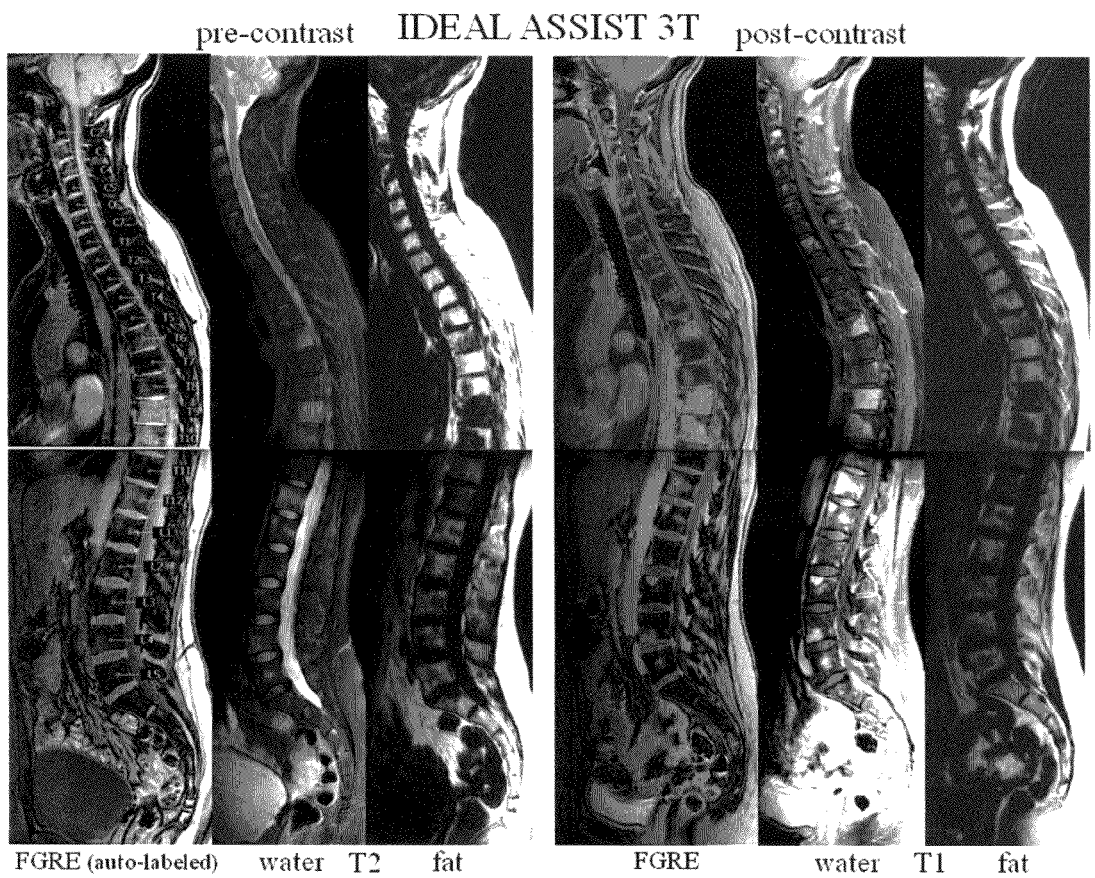
FIG. 24 depicts potential application of spine image labeling technology to fat-water decomposed images.

With a head/neck/spine (HNS) array coil, ASSIST can be extended to include the head and neck as well as the spine. Depending on patient height and the magnet's vertical field coverage, the entire head, neck, cervical, thoracic, and lumbar-sacral spine can now be auto-imaged in 2 or 3 contiguous or slightly overlapping 3D sagittal stations. The head can be imaged with either straight sagittal 3D sequencing and subsequently reformatted or with optimized oblique sagittal 3D sequencing, the latter potentially using the method described in Weiss K L, H. P. Computer Automated Three-Step (CATS) Program for Brain MRI Prescription in Talairach Space for rapidly obtaining a 2D midline sagittal section of the brain. Further, as an alternative to acquiring 7 sagittal 2D sections through the spine with a single GRE sequence, the entire spine can now in the same time be volumetrically imaged with a dual-echo 3D sequence affording subsequent fat-water decomposition. As an example of how fat-water decomposition techniques can be utilized to help identify spinal structures (or other regions of interest in a medical diagnostic image), consider that, with fat-water decomposition techniques, candidate structures of interest can be further classified by % water (W/W+F) signal×100%. Intervetebral discs, brain, cord, and surrounding CSF should approach 100% water signal whereas body fat should approach 0% water signal and bone marrow within skull and vertebrae should have an intermediate % water allowing improved tissue characterization over the initially described single echo out-of-phase GRE technique (as shown in FIG. 23). Applying the ASSIST algorithm to derived water only images would simplify automated disc detection as background fat signal, which often overlaps the range of disc signal, would have already been removed. Alternatively, background signal to include bone marrow which contains both fat and water, might be further reduced by applying the ASSIST algorithm to (W-F) images. Additionally, with posterior subcutaneous fat removed, the readily identified posterior contour of the back is nearer to and more closely parallels the orientation of the spine, permitting a more constrained search for spinal structures including the intervertebral discs. Furthermore, assuming fat and related MRI signal to be uniform throughout the body, identifying voxels containing only fat and correcting for their regional variation, would allow implementation of a global signal correction algorithm which could also facilitate ASSIST. Additionally, a fat % index through the interrogated volume or subsets thereof, could be readily derived to serve as a bio-marker for the subject's lipid status and risk for diabetes and other ailments.

Since the descending aorta would typically be included in volumetric acquisitions of the spine, this important structure could also be auto-identified and analyzed. Like the spinal cord and surrounding cistern to be subsequently discussed, this structure should approach 100% water signal, be tubular in nature and oriented along the vertical axis of the body. It should however have a larger diameter than the spinal canal and typically be situated somewhat anterior and leftward of the spinal canal. Depending on the pulse sequencing utilized and whether contrast is administered, due to flow phenomena or vascular enhancement the aorta often has unique signal characteristics simplifying its detection. For example, if overlapping rather than contiguous sagittal ASSIST stations are obtained and a superior saturation pulse is added to the lower station to suppress incoming vascular flow, then the aorta can be uniquely identified in the region of overlap as the structure which has greater signal without the saturation pulse.

The illustrative algorithm above may be modified to enhance robustness over a wider range of populations, modalities and scan sequences. For example, rather than initially searching for discontinuous structures, (intervertebral discs or vertebral bodies) a MRI algorithm might instead search for the continuous relatively midline and predominately vertically oriented tube-like spinal cord extending from the brainstem to the conus and ending at approximately the L1 level; and a CT-optimized algorithm might search for the non-bone containing spinal canal extending from the foramen magnum (large opening at the skull through which the brainstem passes as it transitions to the cervical cord) to the sacrum. For MRI, the algorithm could continue caudal from the conus by searching for the fluid-filled spinal canal extending to the sacrum. A region growing algorithm such as "regiongrow" (MATLAB) might be employed starting from the readily identifiable brainstem (with MRI) or foramen magnum (with CT) and followed caudal to the sacrum. The idea is to start with a set of "seed" points (which may be automatically placed) and from these grow regions by appending to each seed neighboring voxels with predetermined properties similar to the seed.

Once the course of the spinal cord or canal is identified the search for intervertebral discs or vertebral bodies could be favorably constrained to the appropriate region immediately anterior to the cord/canal and the orientation of the putative intervertebral discs and bodies could be constrained so that they are nearly perpendicular to the long axis of the cord/canal at each level.

Figure 13A:
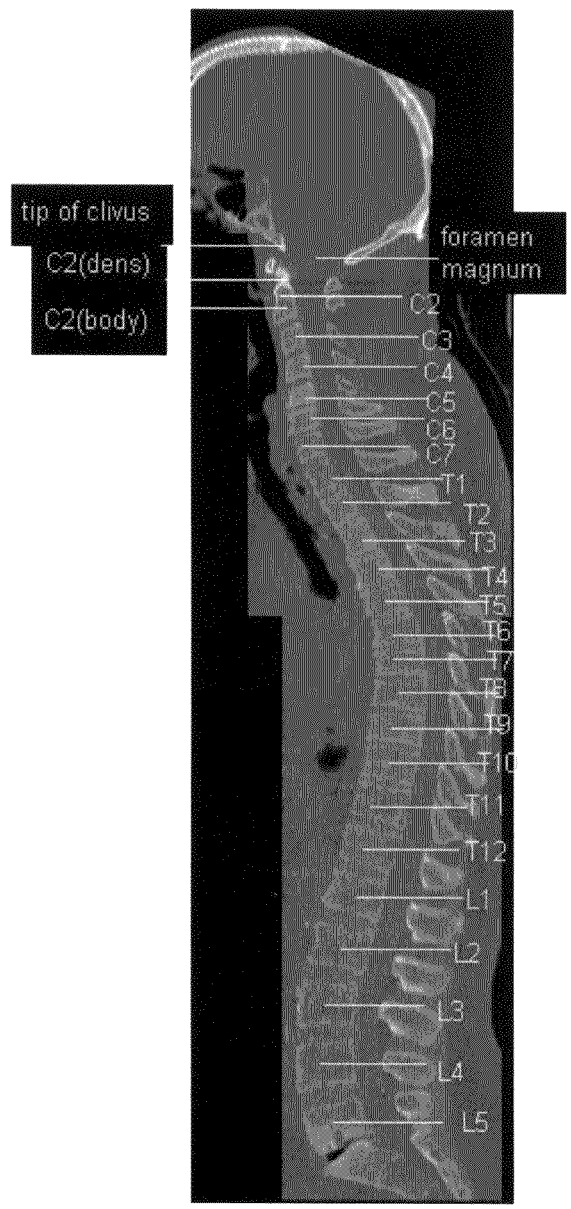
FIG. 13a is a midline sagittal image through the skull and entire spine of a patient auto-generated from a volumetric CT data set with correctly labeled vertebrae using the Automated Spine Survey Iterative Scan Technique (ASSIST) algorithm described herein. Bone optimized reconstruction algorithm utilized and contrast settings also optimized for bone depiction.

Alternatively or additionally, the algorithm could iteratively search for and identify structures from the head caudally to the sacrum. In FIG. 13a for example, the algorithm could first locate the tip of the clivus (anterior aspect of the foramen magnum). As is well known to those of ordinary skill in the art, the head (brain and skull) is a well characterized rigid body, and auto-identification of head structures can be readily achieved on 2D midline sagittal sections or lateral projections (as described in Weiss K L, H. P. Computer Automated Three-Step (CATS) Program for Brain MRI Prescription in Talairach Space. US Office of Patent and Copyright. USA: University of Cincinnati, 2004; Weiss K L, Pan H, Storrs J, et al. Clinical brain MR imaging prescriptions in Talairach space: technologist- and computer-driven methods. AJNR Am J Neuroradiol 2003; 24:922-9 and Weiss K L, Storrs J, Weiss J L, Strub W. CT brain prescriptions in Talairach space: a new clinical standard. AJNR Am J Neuroradiol 2004; 25:233-7.) or from 3D volume data sets, the latter method often employing referential atlases, volumetric matching, and probabilistic determinations (Auto-Align, Cortechs Labs Inc., Charlestown, Mass.; SPM, Wellcome Dept. of Imaging Neuroscience, London, UK; FSL, Analysis Group FMRIB, Oxford, UK).

After auto-locating the tip of the clivus, the algorithm could then search for C2 (dens and body) situated in very close proximity beneath the clival tip. After identifying and perhaps outlining the C2 body, the algorithm could search for the adjacent disc (C2-3) or vertebra (C3) and continue this iterative process caudally until the sacrum is identified. As each vertebra and/or disc is consecutively identified, search parameters for the next level can be modified based on the size and orientation of previously identified structures (vertebrae and discs).

As disclosed for MRI and CT of the brain in the cross-referenced application, direct scanner integration and related algorithms for computer assisted diagnosis could eventually be used in "real-time" automated spine image analysis and iterative scan prescriptions. For example, with MRI, optimally angled axial oblique sequencing could be auto-prescribed through all interspaces or those discs demonstrating abnormal morphology or signal characteristics on the ASSIST or subsequent sagittal sequences. Specific Absorption Rate (SAR) limitations set by manufactures, FDA, or similar international regulatory bodies to reduce body or body part heating may also be mitigated by an algorithm to optimize the order of auto-prescriptions (regions to be covered) so as to allow time for cooling of one region while scanning another. By streamlining and converting Matlab code to C++, algorithm processing time might be significantly shortened. Coupled with an integrated head and spine array coil, rapid computer automated iterative prescription and analysis of the entire neuro-axis may be possible.

Alternatively, or additionally, 3-D sagittal spine sequencing may be obtained. Thus a single 3-D sequence could be substituted for multiple-multi-planar 2-D sequences, which, in the aggregate, are far more time consuming. Using this approach, the volumetric MRI data set or volumetric CT data set could be labeled and then automatically reformatted in optimized planes for visualization of anatomy and pathology. Typically, the three chosen orthogonal planes would be oriented relative to the patient's spinal axis as derived from ASSIST algorithm 100, or modification thereof, rather than conventional auto-generated sagittal, axial, and coronal planes oriented relative to the scanner.

Figure 13B:
FIG. 13b displays the same midline sagittal section through the skull (brain) with "standard" soft tissue-optimized reconstruction algorithm utilized and contrast settings optimized for brain depiction.
Figure 13C:
FIG. 13c displays the same midline sagittal section through the skull (brain) with composite auto-display of the optimized bone (skull) from FIG. 13a and the optimized soft tissue (brain) from FIG. 13b.

In regards to CT or other potentially volumetric imaging techniques, after acquisition of the initial volumetric data set, the ASSIST computer algorithm could be used to prescribe additional sections through specific areas of interest, with different imaging parameters (e.g. kVp, mAs, slice thickness or helical acquisition technique) or in a dynamic mode post contrast administration. Moreover, ASSIST may be used to optimize the reconstruction algorithms (block 6) or field-of-view (FOV) utilized after acquisition of the volumetric data set. For example, in relation to spine imaging, FOV centering or size may be adjusted so as to focus on the spinal elements. A bone-optimized algorithm could be chosen for sections containing bone (e.g. axial oblique sections through the vertebral bodies) and a soft-tissue algorithm could be chosen for sections containing soft tissues (e.g., discs, or the brain as shown in FIG. 13b). Furthermore, composite images may be created such that regions containing bone are displayed with the bone algorithm and those without bone are displayed with the soft-tissue algorithm (FIG. 13c). Additionally, once an algorithm such as described previously has been used to identify bones and soft tissues, those bones and soft tissues can be displayed with independent contrast settings such that the features of the bones and soft tissue are optimally visible. Further, the contrast settings for bones and soft tissues could be independently adjustable, so that a doctor, technologist or other individual examining a reconstructed image could adjust the contrast of the various portions of the image to suit their purposes and preferences.

Another use for detection and labeling algorithms such as described above is the automated production of reports. For example, at the present time, a neuroradiologist examining a picture of a patient's neuro axis can write notes such as that the canal is stenotic (tight). However, utilizing the algorithms described above, a computer can automatically identify various features of the neuro axis, and then write summary reports regarding those features which are much more detailed and clear than is currently possible. For example, the algorithms described above could identify the location of the canal, and produce a report which includes both the precise canal volume and an indication of its relationship to the average canal volume in terms of standard deviations. Similar information could be produced and expressed for any portion of, or structure in, the neuro axis.

Once identified using techniques such as described above, spinal structures can be further auto-characterized in terms of their morphology and tissue characteristics; and subsequently compared to population or individual norms to determine which structures are abnormal or in need of further imaging or treatment. Such characterization and comparison could be used in the generation of reports as described above. Labeling could be used to correlate available image data, and facilitate multi-parametric (spectral) analysis of the identified structures (regions-of-interest) to evaluate tissue characteristics. The technique can facilitate the automated scan prescriptions, real-time lesion detection, and examination tailoring. For example, the techniques described herein could be implemented in automated MRI Detection, Analysis, and Guided-Intervention of Spine Pathology involving vertebrae (fractures, osteoporosis and related fracture risk, malignancy, endplate degeneration—Modic Type I, II, and III changes, facet degeneration) intervertebral discs (degeneration and herniation), spinal canal (spinal stenosis, extramedullary lesions, cord lesions or tethering) and nerve roots (compression or neoplasm). Spine pathology is a leading cause of morbidity and disability in this country. The techniques described herein will improve detection and assessment of disco-vertebral degeneration, osteoporotic and pathologic compression fractures-all potential underlying causes of ubiquitous back/neck pain in this country.

Using advanced MR imaging techniques, the entire spinal axis can be interrogated in the sagittal plane in less than a minute. With this screening data, the vertebral bodies and inter-vertebral discs can be identified and subsequently analyzed with software implementing the algorithms described herein. Based on this initial assessment, regions of suspected pathology to include vertebral fractures and disc herniations, could be further interrogated with more dedicated computer driven prescriptions to confirm and better characterize pathology. If for example, a fracture is identified, additional multi-parametric sequencing through the involved vertebrae could be obtained to determine whether the fracture was related to osteoporosis or underlying malignancy. In some embodiments, the screening data might be obtained by the use of a scout scan, or initial scan. In embodiments where a scout scan is used, regions which were further interrogated would be referred to as regions subjected to detailed scans, that is scans which obtain information not available from the scout scan.

Automated Spine MRI Assessment and Guided Intervention: The techniques described herein can be used to improve current spine screening, assessment, surveillance, and therapeutic intervention. As is known to those of skill in the art, MRI-derived parameters hold promise for improved fracture risk prediction and evaluation of degenerative spine disease (see Wehrli F W, Hopkins J A, Hwang S N, Song H K, Snyder P J, Haddad J G. Cross-sectional study of osteopenia with quantitative MR imaging and bone densitometry. Radiology 2000; 217:527-38). Unfortunately, MRI has been too time intensive and costly to justify as an osteoporosis-screening instrument. It also has lacked accurate parametric quantification of key markers related to spine degeneration and back pain. These shortcomings can be addressed by integrating MRI-derived parameters of bone quality with a novel rapid high-resolution total spine screen (ASSIST).

Figure 20A:
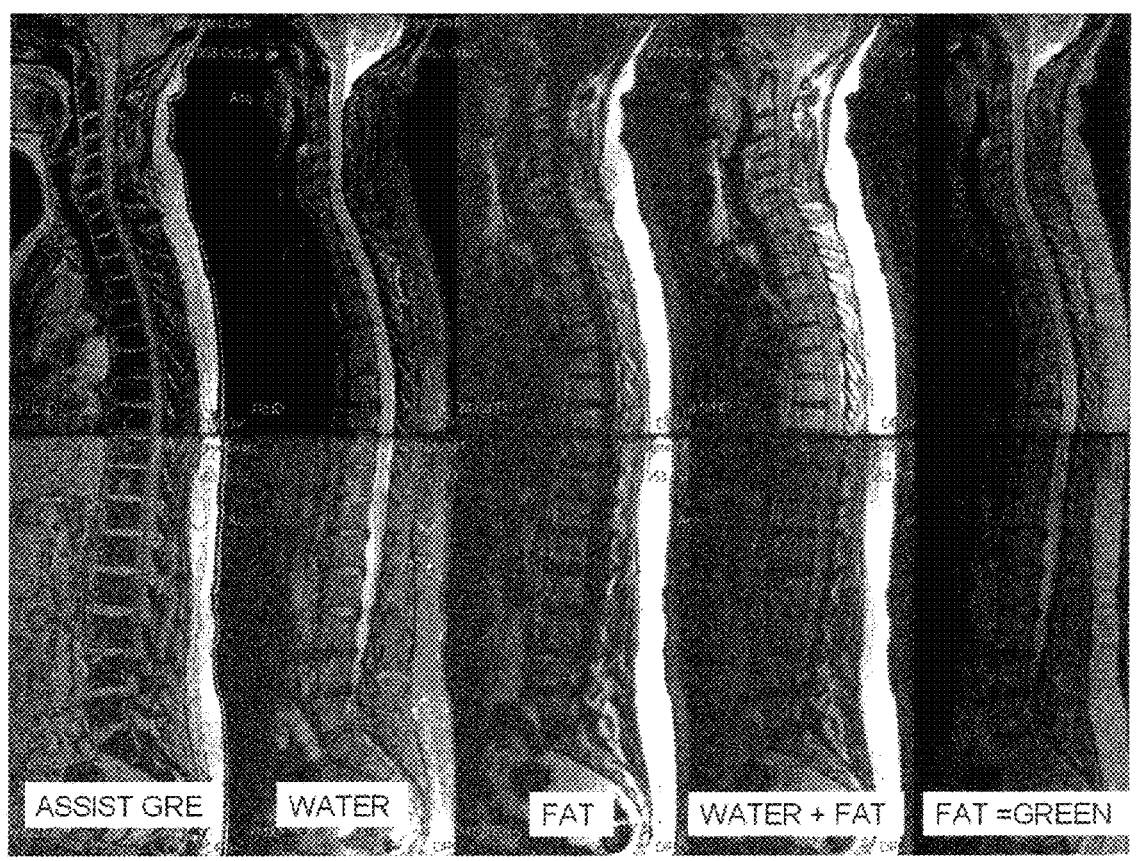
FIGS. 20A-20B demonstrate integration of ASSIST with IDEAL for improved multi-spectral tissue characterization.
Figure 20B:
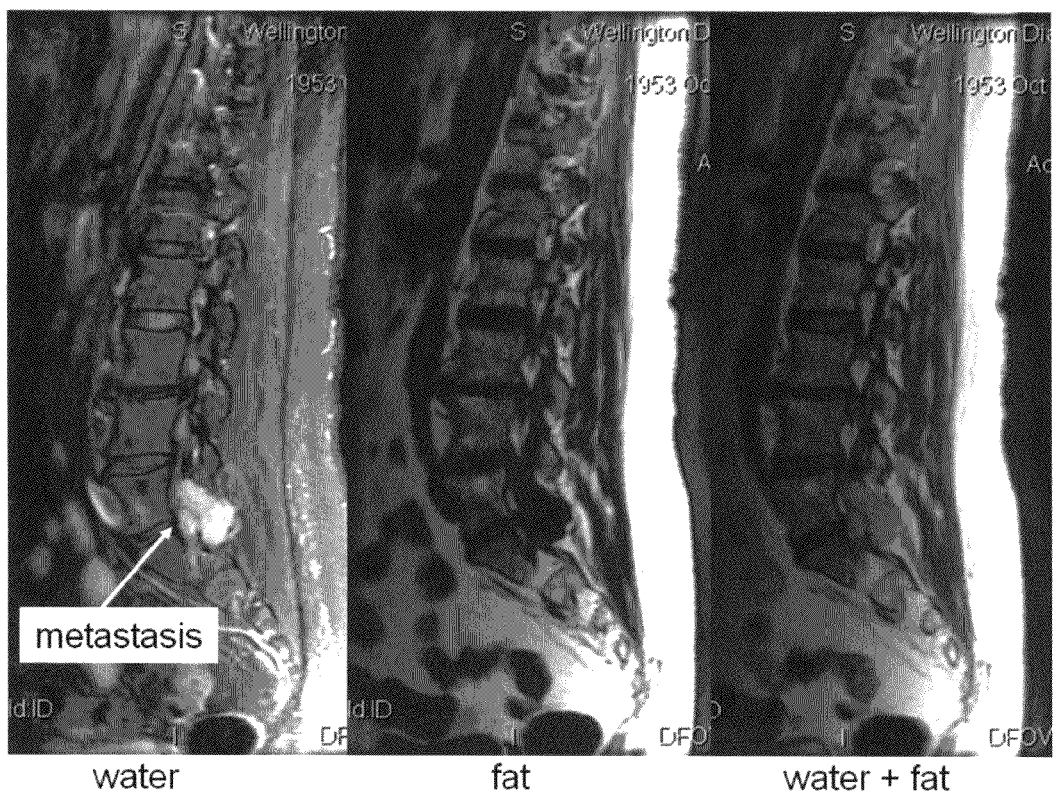
Figure 21:
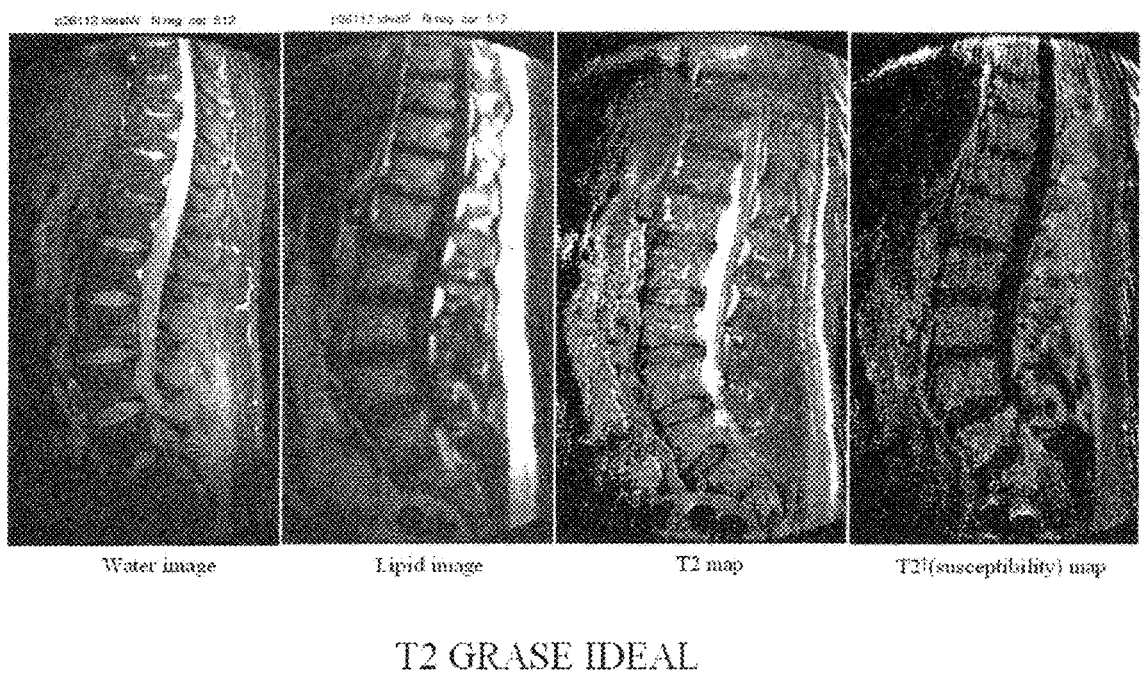
FIG. 21 depicts additional multi-parametric maps derivable from GRASE IDEAL.

In particular, the ASSIST technique described above can be integrated with fast dual GRE (e.g., as described in: Ma J. Breath-hold water and fat imaging using a dual-echo two-point Dixon technique with an efficient and robust phase-correction algorithm. Magn Reson Med 2004; 52:415-419), spin-echo and GRASE (Gradient and Spin-Echo Imaging) versions of an imaging technique termed iterative decomposition of water and fat with echo asymmetric and least square estimation (IDEAL). (FIGS. 20A, 20B, and 21). The GRASE IDEAL technique provides T2, T2*, and T2† maps as well as the typical water, fat, and composite (water plus fat) images. These MRI-derivable parameters may be helpful in achieving the aforementioned specific aims. For example, T2I represents cancellous bone-induced intravoxel dephasing and is negatively correlated with fracture risk. ASSIST integrated with GRASE-IDEAL (FIG. 21) or other multiparametric derivable MRI sequences provides efficient automated screening and assessment of post-menopausal women at risk for osteoporotic or pathologic spine fractures and/or presenting with back pain. This integration promotes patient care by providing improved risk assessment, identification and characterization of vertebral fractures; improved assessment of spine degeneration-back pain; and metastatic disease; and improved image-guided therapeutic management as well as facilitate related image-guided procedures in conjunction with a MRI-compatible robotic arm and aforementioned interventional spine array coil. The technique of integrating MRI Automated Spine Survey Iterative Scan Technique (ASSIST) can be used to provide quantitative assessment of sub-endplate degenerative/stress related Modic Type 1, 2, and 3 changes. Additionally, the integrated MRI Automated Spine Survey Iterative Scan Technique (ASSIST) can be used to provide quantitative assessment of fatty bone marrow replacement for early detection of metastatic disease in the spine and differentiation of osteoporotic from pathologic fractures. Further, ASSIST adaptations will enable real-time MRI-guided vertebroplasty, biopsy, and epidural injections.

Figure 22A:
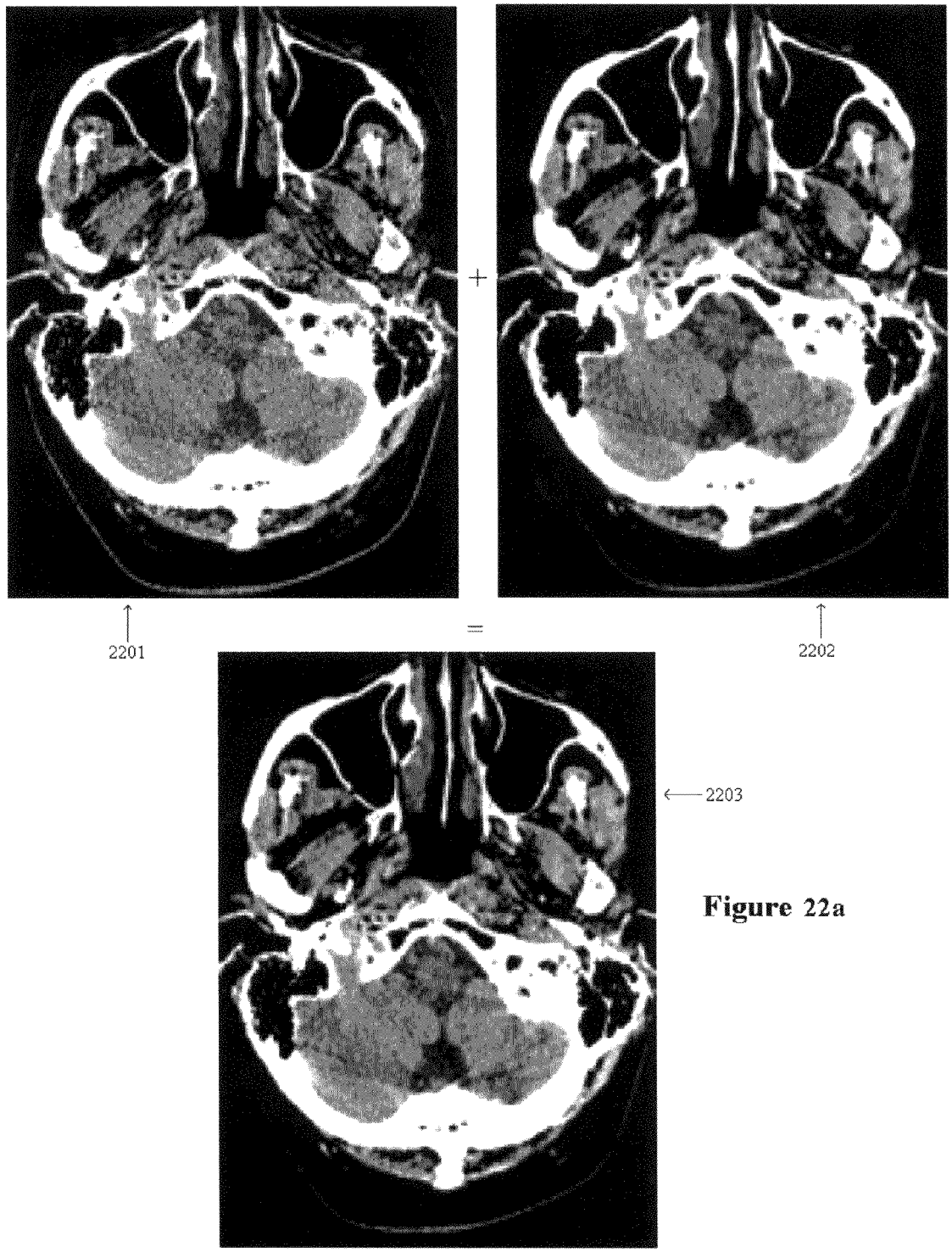
FIGS. 22*a*-22*b* depicts how multiple images can be combined to create a third image while maintaining the details from the two underlying images.
Figure 22B:
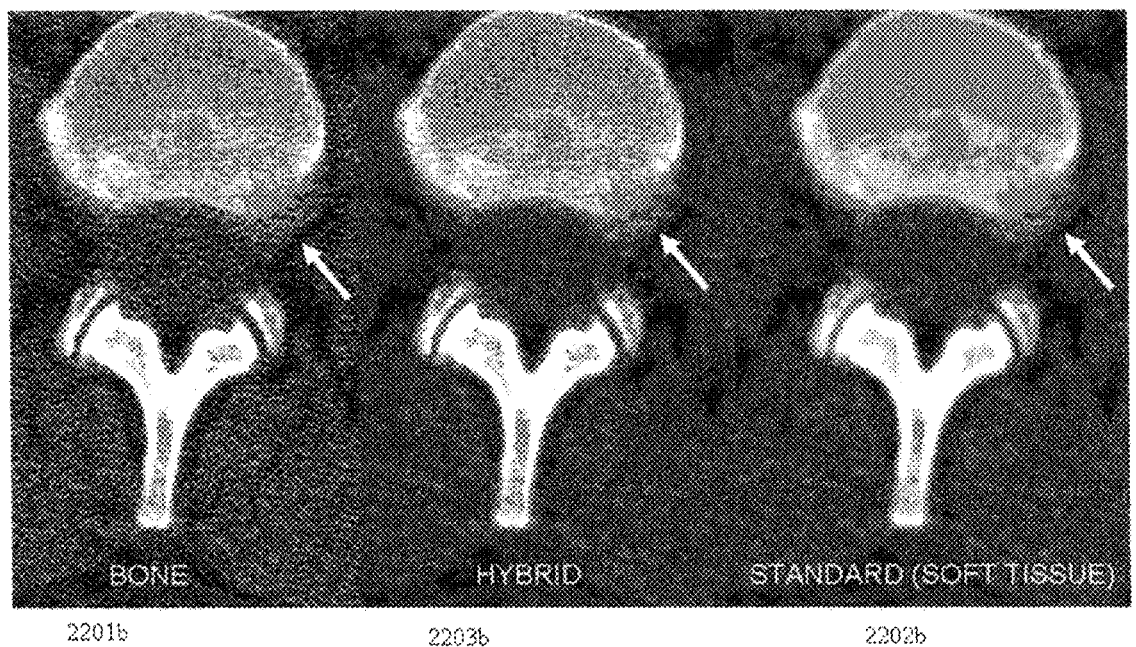

A further technique which can be applied with beneficial effects in the presentation of images is the combination of multiple images in such a manner as to obtain a single resulting image. For example, in the case of a CT scan of a patient's head, it is possible to obtain an image which accurately depicts details of both the patient's skull and brain by combining two co-registered images derived from the same CT source data but created with two different convolution kernels: a first convolution kernel with a high pass filter algorithm for the skull, and a second convolution kernel with a low pass filter algorithm for the brain. This combination might take place by beginning with two images (one created with the first convolution kernel and one created with the second convolution kernel) and, in the image created with the second convolution kernel, replacing pixels having HU values outside the range of −150 and 150 with corresponding pixels from the image created with the first convolution kernel, thereby creating a third image which displays the details from the skull (captured using the first convolution kernel) and from the brain (captured using the second convolution kernel). An illustration of this is provided in FIGS. 22a and 22b, where an image created with a convolution kernel having a high-pass filter algorithm [2201] [2201b] and an image created with a convolution kernel having a low-pass filter algorithm [2202] [2202b] are merged to create a third image [2203] [2203b] which includes the most detailed portions of the other two figures. In this way, instead of having to examine two separate images, a doctor could examine only a single image, thereby facilitating the processes of diagnosis and treatment. With Reference to FIG. 22b, note the hybrid reconstruction kernel demonstrates both bone and soft tissue definition as well as the bone and standard reconstruction kernels respectively. Arrow Points to HNP.

It should be understood that the description of image combination set forth above is not intended to be an exhaustive recitation of techniques which could be used to combine medical diagnostic or other types of images. For example, while the above discussion focused on the combination of images for the head, the same techniques can be successfully applied to combine images taken of the lungs and spine, and could be applied to other areas of the body as well. Similarly, while the discussion above disclosed replacement of pixels with HU values outside the range of −150 and 150, other ranges could be used as well. For example, ranges with a minimum value of −150+/−75 HU, and maximum values of 150+/−75 HU could also be used (e.g., from −200 to 100 HU), for example, depending on the material depicted (e.g., type of tissues) in the images being imaged, and the particular hardware used to obtain the images. Also, while the discussion above focused on the combination of images created with different convolution kernels, combining images is not limited to combining images created with different convolution kernels. For example, when a CT machine obtains data sets at different energy levels, the data sets obtained at different energy levels can be combined as well. For instance, if the CT machine obtains data at 140 and 80 kvp levels, then those data sets can be combined at a factor of 0.70/0.30. It is also possible that more than two images could be combined. For example, in some cases there might be images created using three (or more) different reconstruction kernels, in which case a composite image could be created the pixels from the first image having a first set of values, with pixels from a second image having a second set of values, and pixels from a third image having a third set of values. It is also possible that images could be combined simply by averaging pixels values in a series of adjacent slices to get a composite slice reflecting data collected from the entire scan area.

Figure 25A:
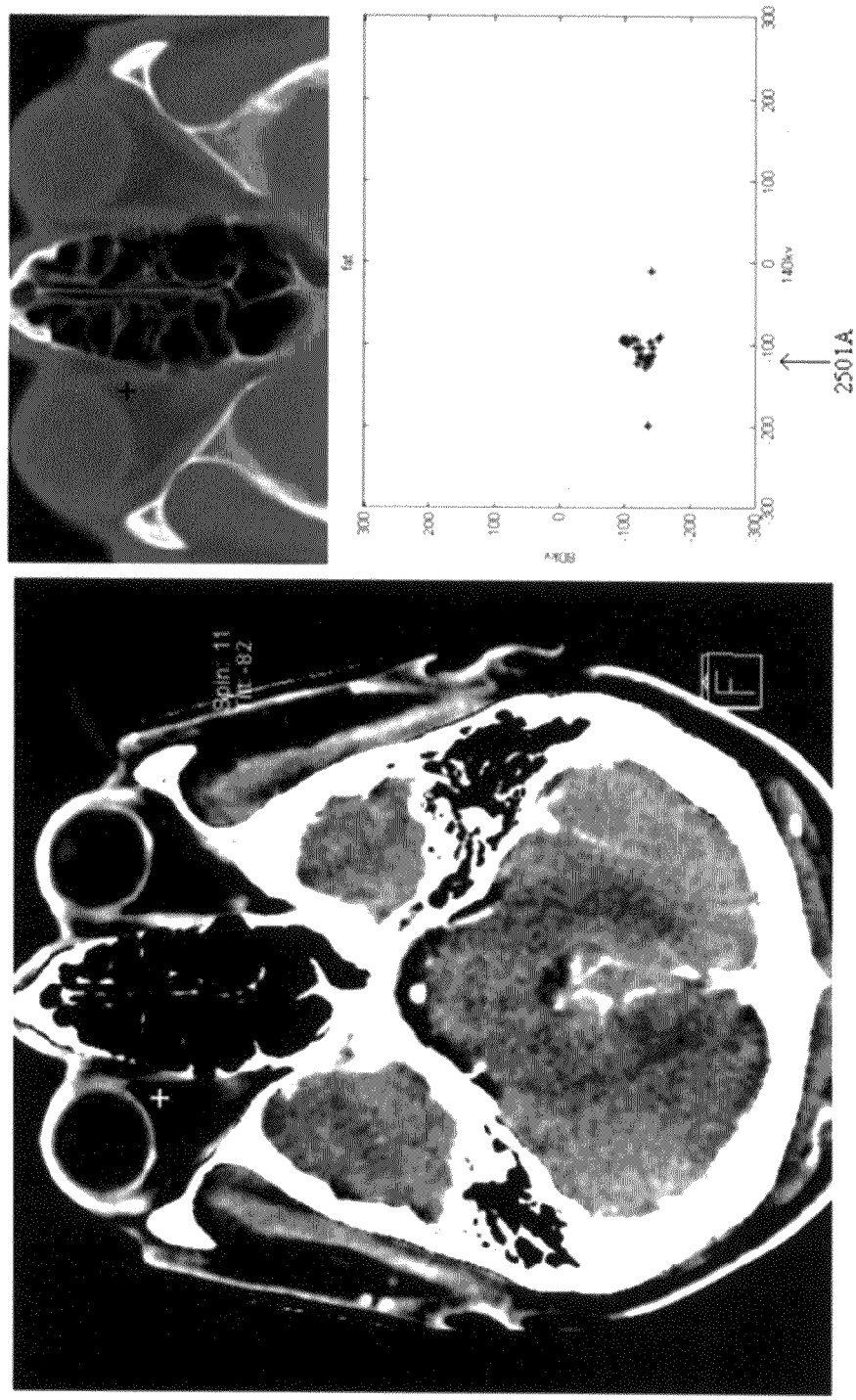
Figure 25D:
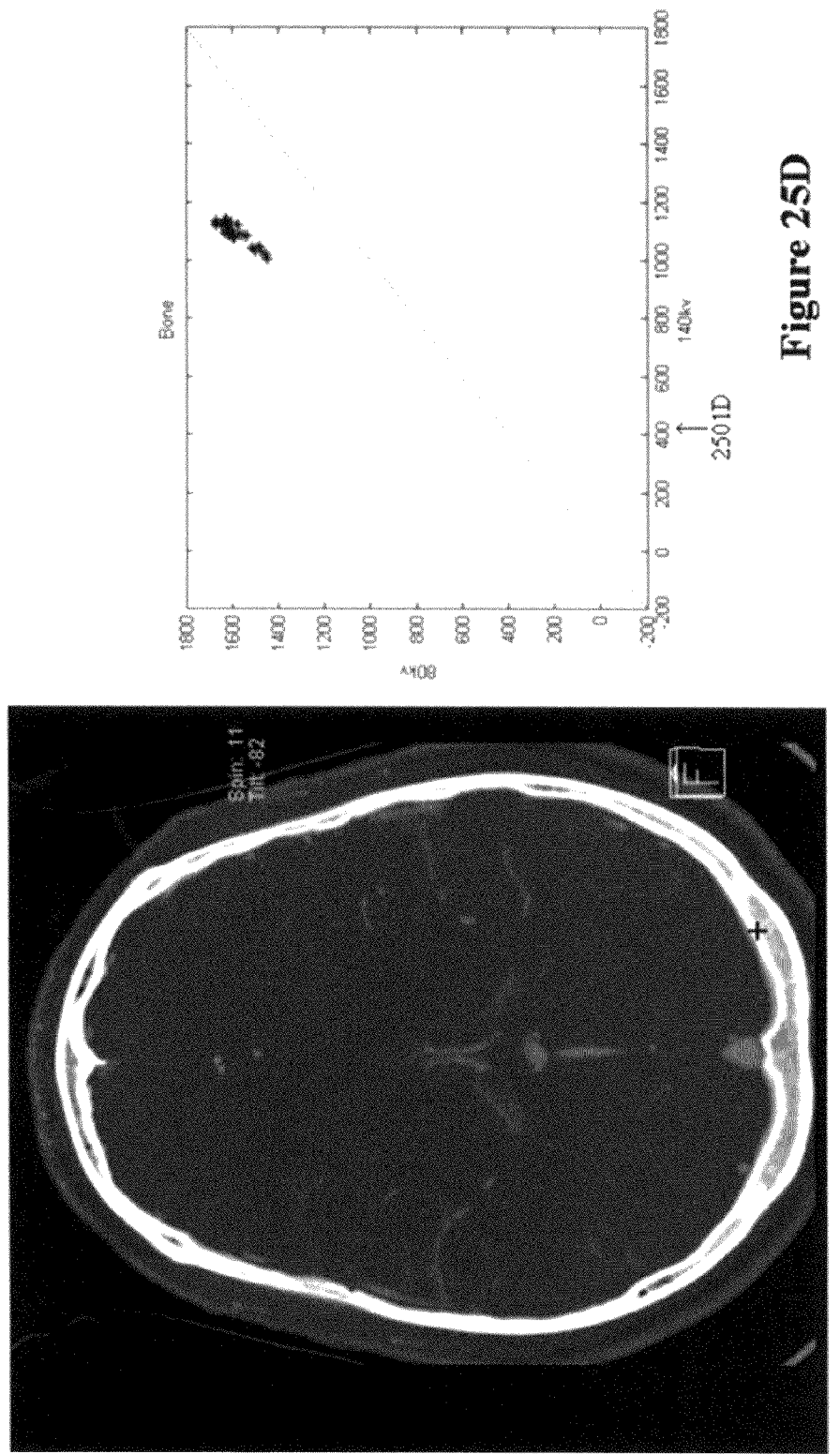
Figure 25E:
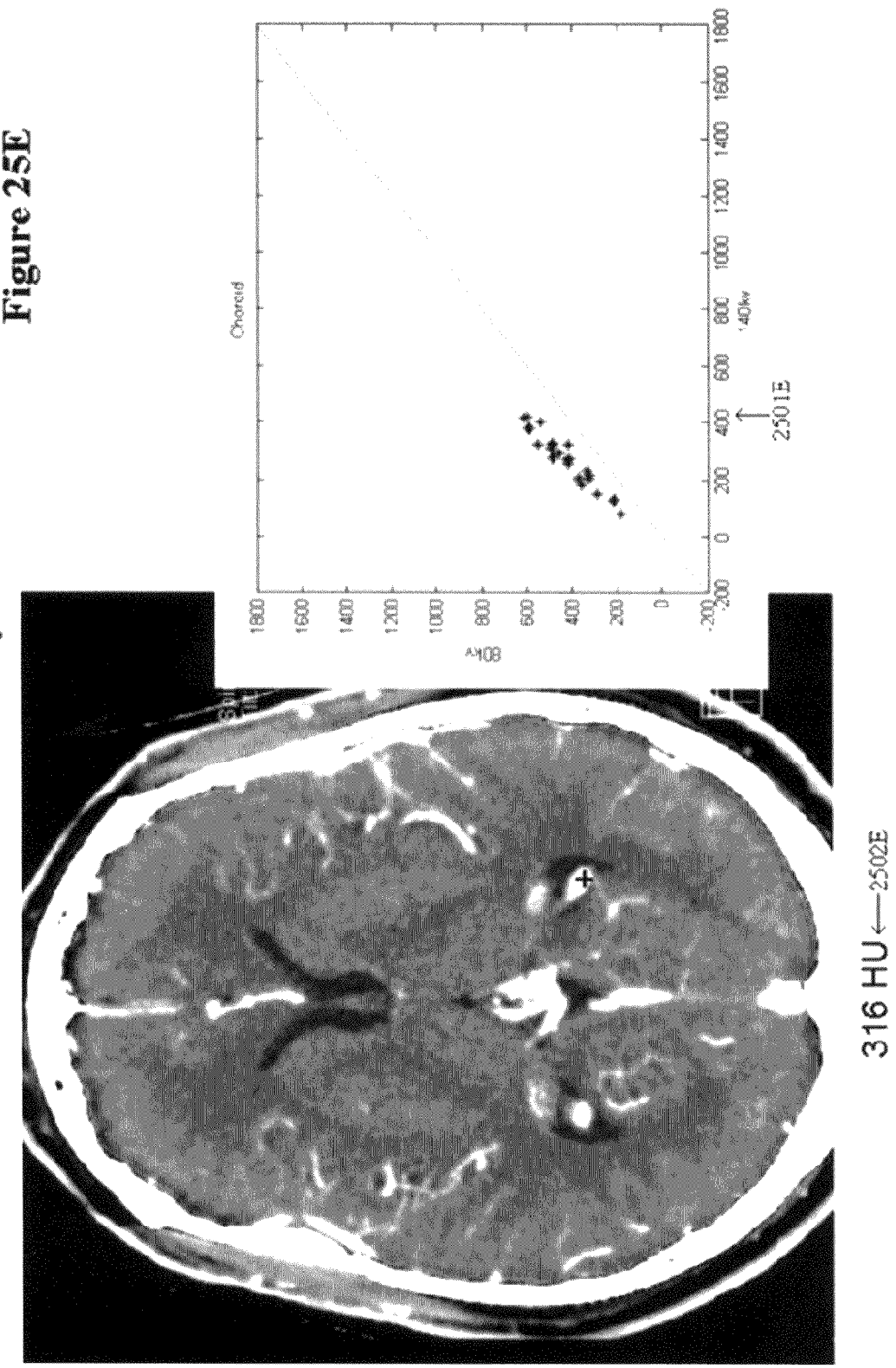
Figure 25F:
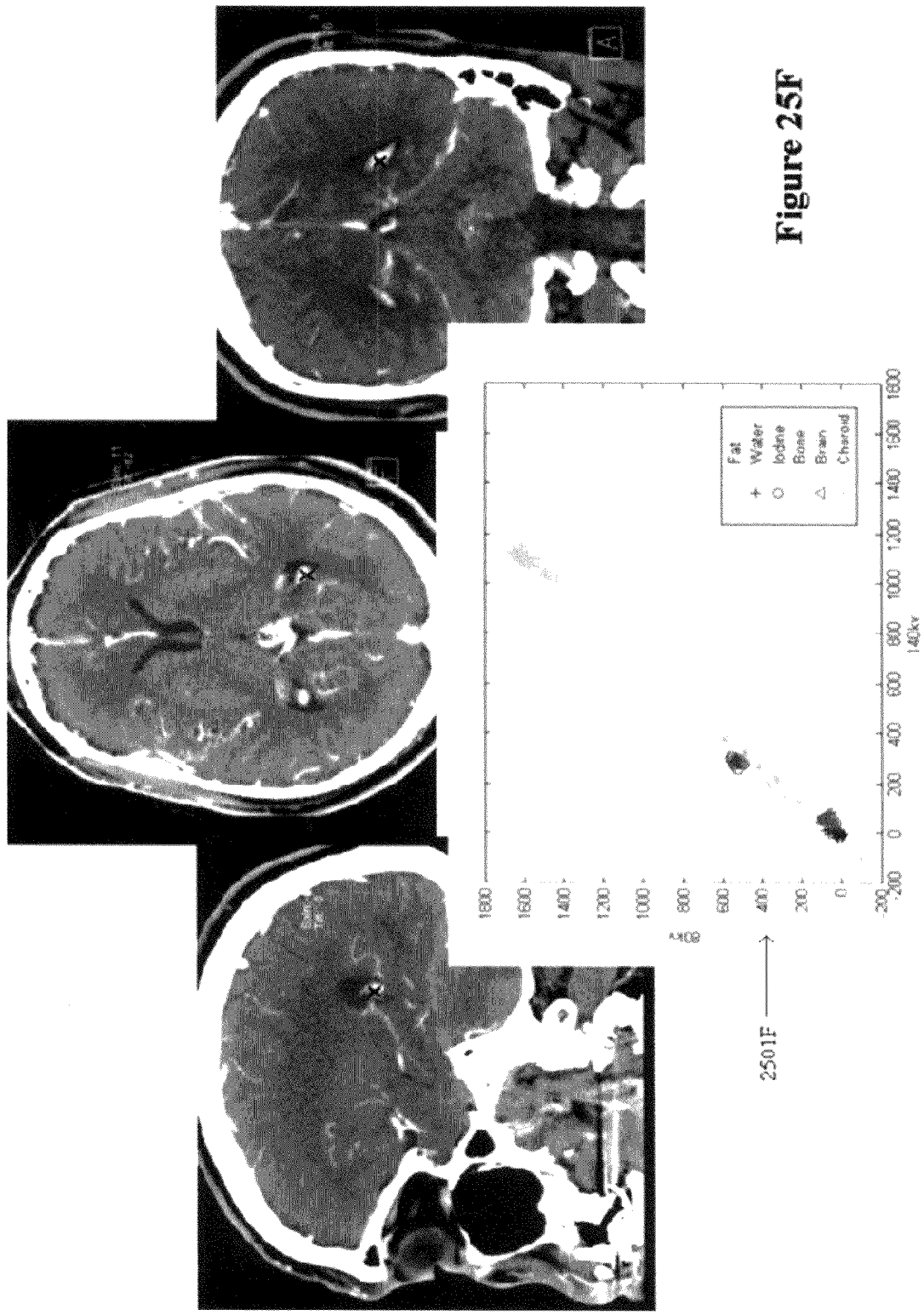

Of course, the approaches described above are not mutually exclusive. For example, in one application of image combination, volumetric dual energy CTs obtained from hard palate to vertex at 80 and 140 kvp, approximately 15 cm coverage, were reconstructed in the axial plane at 0.6 mm intervals using both high pass and low pass convolution algorithms. A hybrid convolution kernel (HCK) which combined high and low pass algorithms as described above was applied to reduce data sets by a factor of two and the 80 and 140 kVp data sets were combined at a 0.30/0.70 ratio to further reduce data sets by a factor of two and optimize contrast vs S/N. The reduced volumetric data set was then semi-auto or auto-reformatted to approximate tri-planar Talairach space manually, identifying two similar contralateral points (e.g. round window basal turn of cochlea) on source axial images, generating the sagittal plane equidistant from these points, identifying the hard palate on this roll and yaw corrected midline sagittal image, and angling 12 degrees; or having the computer auto-identify the sagittal plane optimally bisecting the volumetric data set and auto-identifying the hard palate. Similarly, 2 mm coronal maxillofacial CTs were auto-generated perpendicular to the hard palate. Using volumetric dual energy HCK data sets stored in the computer, ROIs placed on the reconstructed data sets could then be deconvolved and displayed as 2-D HU scatter plots, the two axes being 80 and 140 kVp, with each point corresponding to a voxel within the selected 3D ROI. The ROI itself could be determined in a number of manners, such as by the selection of a single voxel in a presented image, the selection of a region in a presented image, the selection of a voxel and its closest neighbors in an image, the selection of a voxel and its closest neighbors and their closest neighbors, etc. Conversely, in some implementations a scatter plot presentation interface could be designed so that, in response to a user selecting a point on the scatter plot, the computer would interactively display its origin on orthogonal triplanar reformations passing through this voxel. Examples of scatter plots which could be shown using this approach are shown in FIGS. 25A-25E. In those figures, the region of interest is a voxel (shown as a cross) with a single intensity (2502A-2502E, in FIGS. 25A-25E, respectively) as shown in the presented image. However, in those figures, while the ROI has a single intensity as displayed, the scatter plots (2501A-2501E in FIGS. 25A-25E, respectively) show that the ROI is actually made up of a substantial amount of underlying data. FIG. 25F shows a combination of the scatter plots from FIGS. 25A-25E (combined scatter plot is labeled 2501F), and also shows how a ROI (displayed as an X) can be presented simultaneously in three orthogonal images, so that a radiologist or other individual examining the images can pinpoint the location of the ROI in 3-Space. The result of this approach was to obtain 5 mm Talairach axial brain images wherein the data set to be reviewed was reduced by a factor of 2×2×8=32; so that the 1,000 images generated were culled to 31 and approximated routine non-volumetric head CTs (5 mm sections angled 12 degrees from hard palate by adjusting gantry) and MRIs (angled parallel to the AC-PC line after role and yaw correction) which are routinely performed in the art.

While the technologies described were initially developed for medical imaging, they may also be applied to industrial or other usage. For example, analysis of dual-energy x-rays or CT scans of inanimate objects, such as luggage, may be enhanced by the HCK and deconvolvable 2-D scatter plot technology described herein. For example, using the combination of images created with different convolution kernels in the context of luggage screening, there might be a first convolution kernel which is particularly adapted to detecting and displaying dense objects, such as firearms, while there could be a second convolution kernel which is particularly adapted to detecting and displaying organic material, such as might be found in an explosive. By the adaptation of techniques such as described above, the process of screening luggage for weapons and explosives could be made more efficient, thereby improving the security and convenience of air travel. Of course, it should be understood that this example is provided as an illustration only, and that other approaches described herein (e.g., two dimensional scatterplots with mapping back to original slices) could also be applied in areas outside of medical imaging. Thus, in no event should the examples and explanations provided be treated as implying limitations on the scope of any claims included in this or any related applications.

Yet a further technique which can be beneficially applied to the creation, presentation and processing of images is the utilization of a skin/surface marking system to provide spatial reference information. In one version particularly applicable to the medical field, a point localizer 500 such as shown in FIGS. 14A-14I is constructed to include a detectable region affixed to an adhesive fabric strip with corresponding markings so that after application to, and imaging of, a patient, the localizer can be removed with skin marking remaining. It should be understood that the detectable region is the portion of the localizer that generates an identifiable representation in a medical diagnostic or other type of image. As will be discussed below, a detectable region is preferably, though not necessarily, multimodality compatible. In the case of a localizer such as shown in FIGS. 14A-14I, the localizer can also be constructed to directly adhere to a patient's skin. Alternatively, an ink or dye could be added to the adhesive/undersurface of the localizer to directly mark/imprint the skin obviating the fabric strip. For MRI and CT a detectable region could comprise a small loop of tubing which could be filled with a radioattenuative solution (e.g. containing iodine) doped with a paramagnetic relaxant (e.g. $CuSO4$, $MgSO4$, Gd-DTPA). Alternatively, the tubing itself may be radiopaque for optimal CT visualization. For nuclear imaging to include planar scintigraphy, SPECT and PET, the detectable region might include a port to allow filling with the appropriate radionuclide. While the above localizers would be visible with planar radiography, a fine wire circle or dot (e.g. lead, aluminum) could also be utilized as a detectable region with this modality given its very high spatial resolution. Other shapes and corresponding adhesive markings could be utilized to discriminate different foci and/or add further localizing capability. Additionally, an activatable chemiluminescent mixture could be added for thermography, optical imaging, light based 3D space tracking or simply improved visualization in a darkened environment.

In the second major detectable region configuration, a unique cross shaped grouping of prefilled or fillable tubing is utilized as a grid for cross sectional imaging with the number and position of tubes imaged in the axial or sagittal planes corresponding respectively to the slice's z or y distance from the center. In this configuration, each tubing might be constructed as a different section of the detectable region. For planar radiography, a flexible radiopaque ruled cross shaped grid can be employed as a detectable region. Both grids are removable from similarly ruled cross shaped adhesive strips after patient application and imaging.

As a third example of a detectable region, a unique essentially planar grid/phantom is described which may be of flexible construction and reversibly affixed to an adhesive/plastic sheet with corresponding grid pattern for skin marking and to serve as a sterile interface between patient and reusable grid/phantom. The grid/phantom may also be directly adherent to the skin for guided aspiration or biopsy with the cross sectionally resolvable spatial reference in place. A diagonally oriented prefilled or fillable tube overlies a grid like lattice of regularly spaced tubing so that slice location and thickness can be readily determined in the axial and sagittal planes. Additionally, the spatial accuracy of the imaging modality could be assessed and, if individual tubes are filled with different solutions, as might be the case in instances where the different tubes are different sections, multipurpose references for MR/CT, and nuclear imaging could be achieved. Furthermore, if the tubing is surrounded by a perfluorocarbon or other uniform substance without magnetic susceptibility, MR imaging could be improved by reducing skin/air susceptibility and motion artifact. Additionally, the grid/phantom could be incorporated in routinely utilized pads and binding devices with or without skin adhesion and marking.

Figure 14A:
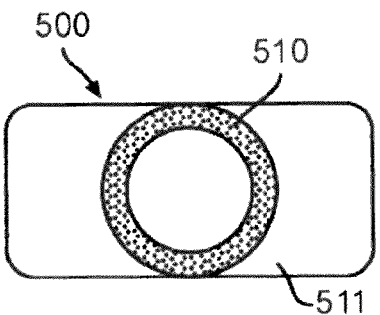
FIGS. 14A-14I are diagrams of a point localizer.
Figure 14B:
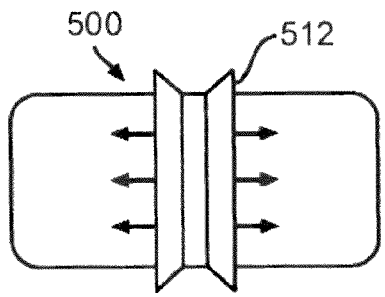

Returning to the drawings, FIGS. 14A-14I depict an illustrative version of a point localizer 500. In FIG. 14A, a loop of prefilled tubing 510 (i.e., a tubal lumen shaped into a tubal ring) is shown superimposed on and reversibly affixed to an underlying medical grade fabric 511, which may double as an adhesive bandage to both cover and mark a wound or puncture site. The diameter of the tubular ring 510 may be 2 cm mid luminal, as illustrated, or outer luminal, as perhaps preferable for integration with the cross shaped grid configuration. Other sized rings, to include in particular a 1 cm. diameter, may also have merit. The tubal lumen should measure 2-5 mm in cross sectional diameter. Cross sectional images through the ring will have characteristic and quantifiable appearances depending on slice thickness and distance from the center. A thin slice through the loop's center, for example, would demonstrate 2 circles of luminal diameter whose centers are separated by a distance equal to the ring's diameter.

The tube lumen can be filled with an appropriate concentration of an iodinated contrast agent for optimal CT visualization doped with a paramagnetic relaxant such as $CuSO4$, $MgSO4$, or GdDTPA to maximize MRI signal via preferential T1 shortening. Alternatively, the tubing itself may be optimally radiopaque for CT, obviating the iodinated contrast. If desired, for optical imaging, thermography, light based 3D space tracking, or improved visibility in a darkened environment, one could add an activatable chemiluminescent mixture whose critical reagents are separated by a membrane readily breached by external force applied to the ring.

Figure 14C:
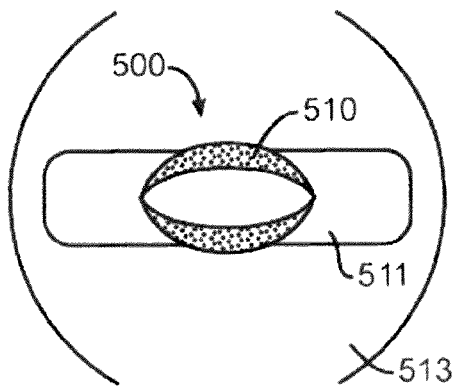
Figure 14D:
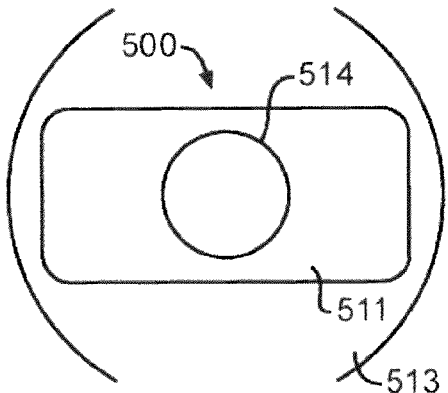
Figure 14E:
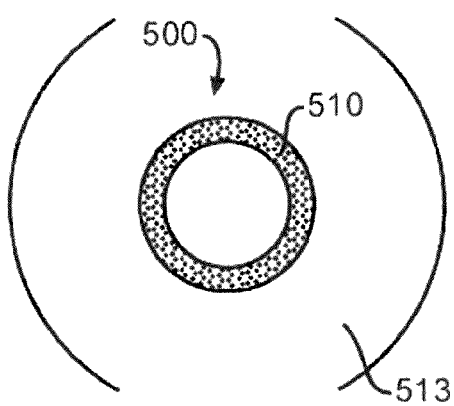

A slightly redundant backing 512 is provided for the adhesive side of the fabric 511 to facilitate peeling (FIG. 14B arrows) and skin placement. With backing 512 removed, the unit 500 adheres to skin 513 as depicted in FIG. 14C. After imaging, the loop 510, which has its own adhesive undersurface, may be removed revealing an underlying fabric marking 514 as in FIG. 14D. The upper surface of the fabric, or circumscribed area thereof, may also have adhesive backing-like properties to facilitate detachment of the loop 510. Once separated from the fabric, the loop 510 could also directly adhere to the skin 513 as in FIG. 14E. Additionally, the adhesive undersurface of the ring could contain a medical grade dye or ink so that a corresponding imprint would be left on the skin 513 after removal, potentially obviating the fabric marker.

Figure 14F:
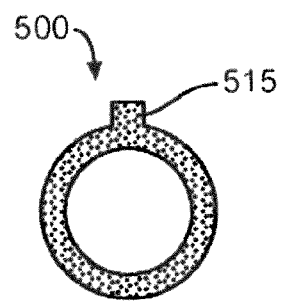

A port 515 may be directly integrated into the tubular ring 510 as in FIG. 14F, and a vacuum created within the lumen to facilitate filling at the imaging center. This feature could be beneficial for radionuclide scans and add flexibility for other imaging studies. Alternatively, the detectable region might comprise a virtual space within a composite plastic sheet. Such a detectable region could be created by adhering two plastic sheets to one another, but allowing a region of sheets (the virtual space) to remain separable so that it could later be filled in a manner similar to the tubing discussed above. Such use of a virtual space would not require the manufacture with a vacuum, because a virtual space, unlike a tube, does not ordinarily have any contents.

Figure 14G:
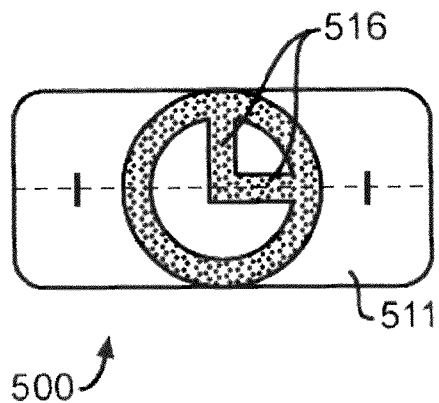
Figure 14H:
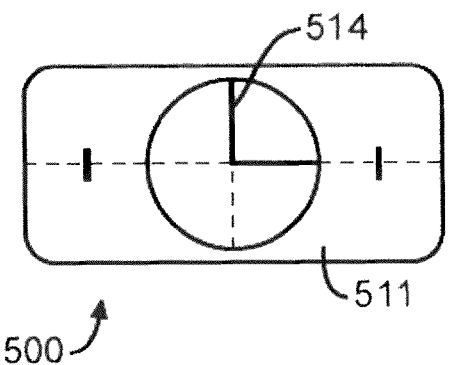

To increase spatial reference capability and allow multiple localizers to be discriminated from each other, the detectable regions such as the ring and underlying fabric marking may be modified as in FIGS. 14G and 14H. As illustrated, two tubular spokes 516 at right angles to each other may be added with luminal diameter less than or equal to that of the loop. Typically, the modified ring would be positioned on the patient so that the spokes are aligned at 0 and 90 degrees as perhaps determined by the scanner's alignment light. Subsequent rings could be progressively rotated 90 degrees so that quadrants I, II, III, and IV are sequentially subserved by the spokes. With the simple ring included, this would provide 5 distinguishable localizers. Moreover, if stacking of two rings is utilized, 30 (5×6) distinguishable localizer configurations are possible. Suggested numbering would employ the base 5 system, assigning the simple ring the value 0 and each modified ring the value of the quadrant subserved.

Figure 14I:
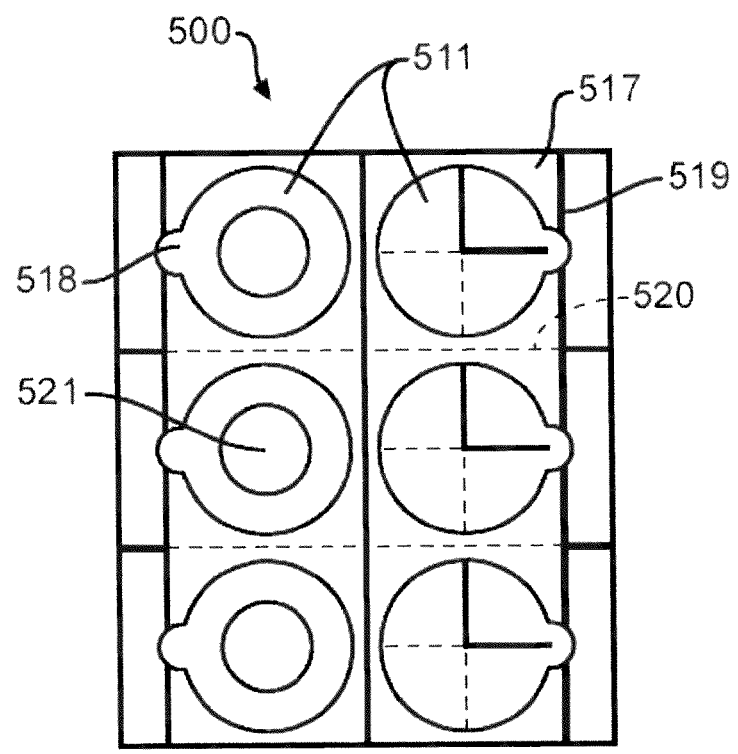

Multiple localizers may also be dispensed on a single sheet rather than individually packaged. FIG. 14I illustrates such a sheet, demonstrating adhesive backing 517 and overlying fabric 511 with the simple ring (left side) and modified ring (right side) localizers removed. Tabs 518 have been added to the fabric to facilitate both removal of the unit from the backing and the localizer from the fabric. Discontinuity of the backing (solid lines 519) underlying the tabs would also simplify removal of the fabric from the backing and perforations through the backing (dotted lines 520) would facilitate separation of individual units from each other. If desired, a smaller diameter (e.g. 1 cm) ring and associated backing albeit without tab could be placed within the central space (521) bordered by the simple ring fabric 519.

Figure 15A:
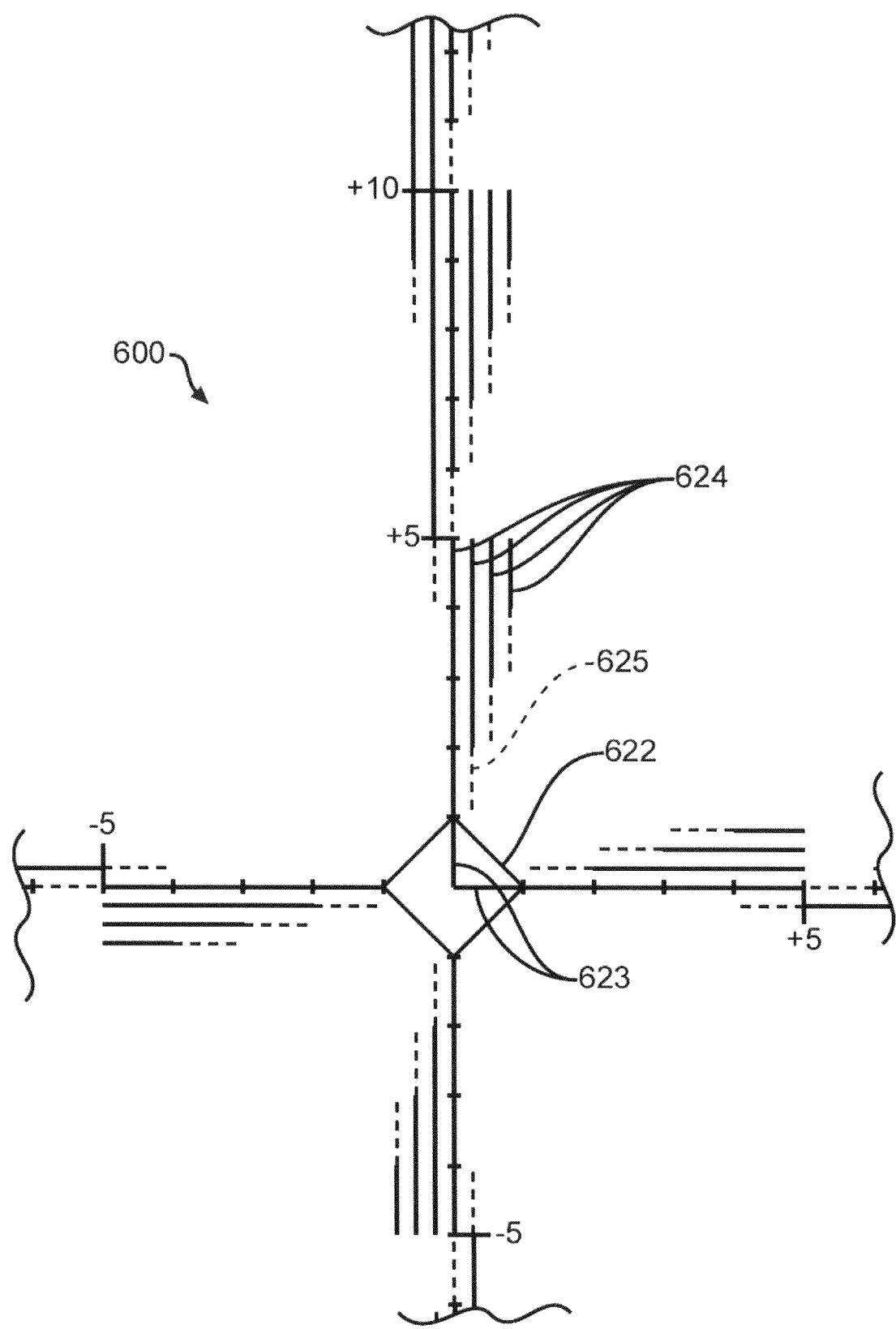

Embodiments of a prefilled or fillable cross shaped localizer grid 600 are illustrated in FIGS. 15A-15F. In FIG. 15A, a modified tubular square 622 with diagonal dimensions of 2 cm and containing 2 smaller caliber spokes 623 at right angles to each other serves as the hub. Uniquely positioned rows of tubing (624) radiate from each corner along the vertical and horizontal axes. The luminal diameter of the radiating tubes is uniform and on the order of 2 mm except where indicated by dotted lines 625 corresponding to gradual tapering from 0 to the uniform diameter. Depending on the distance from the central hub, 1 or 2 rows of tubing will be present with up to 4 tubes in each row as best illustrated in a table of FIG. 15B. The lower row of tubes (i.e. closest to skin) would correspond to increments of 1 cm and the upper row to increments of 5 cm so that a maximum distance of 24 cm would be denoted by 2 full rows. To indicate positive distances, the tubes are progressively ordered from left to right or down to up with the reverse true for negative distances as illustrated in FIGS.

15A-15B. Fractions of a centimeter would be indicated by the diameter of a cross section through a tapered portion of tubing divided by the full uniform diameter.

Figure 15C:
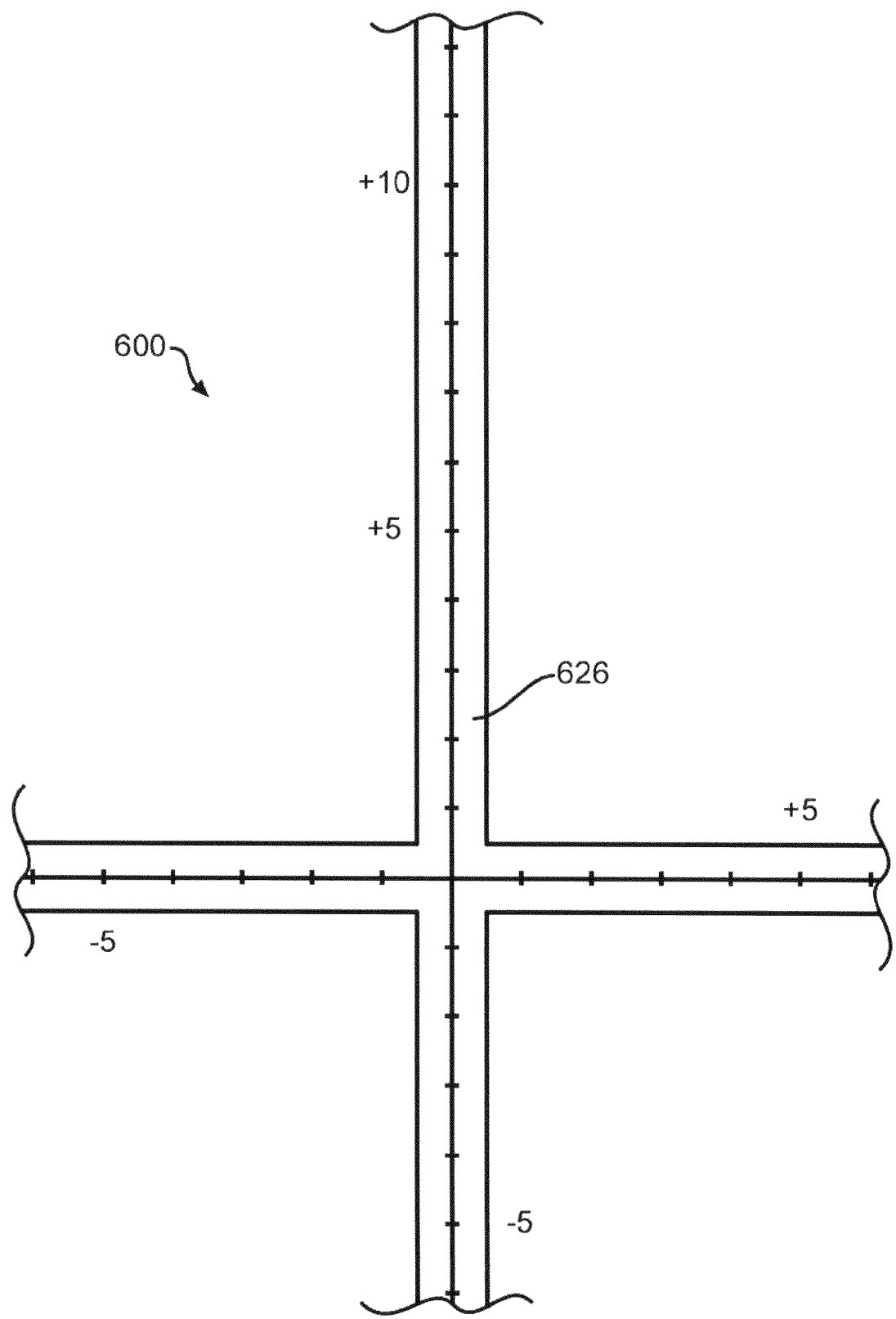

The cross-shaped grid of tubing is reversibly affixed to a medical grade adhesive fabric 626 with corresponding markings and backing. The fabric 626 is illustrated in FIG. 15C with the overlying tubing removed. The grid and associated fabric may come as a single cross-shaped unit or as a modified square and separate limbs which could be applied to the patient individually or in various combinations. Modified squares could also link whole units and/or individual limbs together to expand coverage, with 25 cm. spacing between the center of adjacent squares. The tubing may be flexible to allow the limbs to conform to curved body contours such as the breast. Additionally, either the limbs could be readily truncated at 5 cm. intervals or be available in various lengths for optimal anatomic coverage.

Figure 15D:
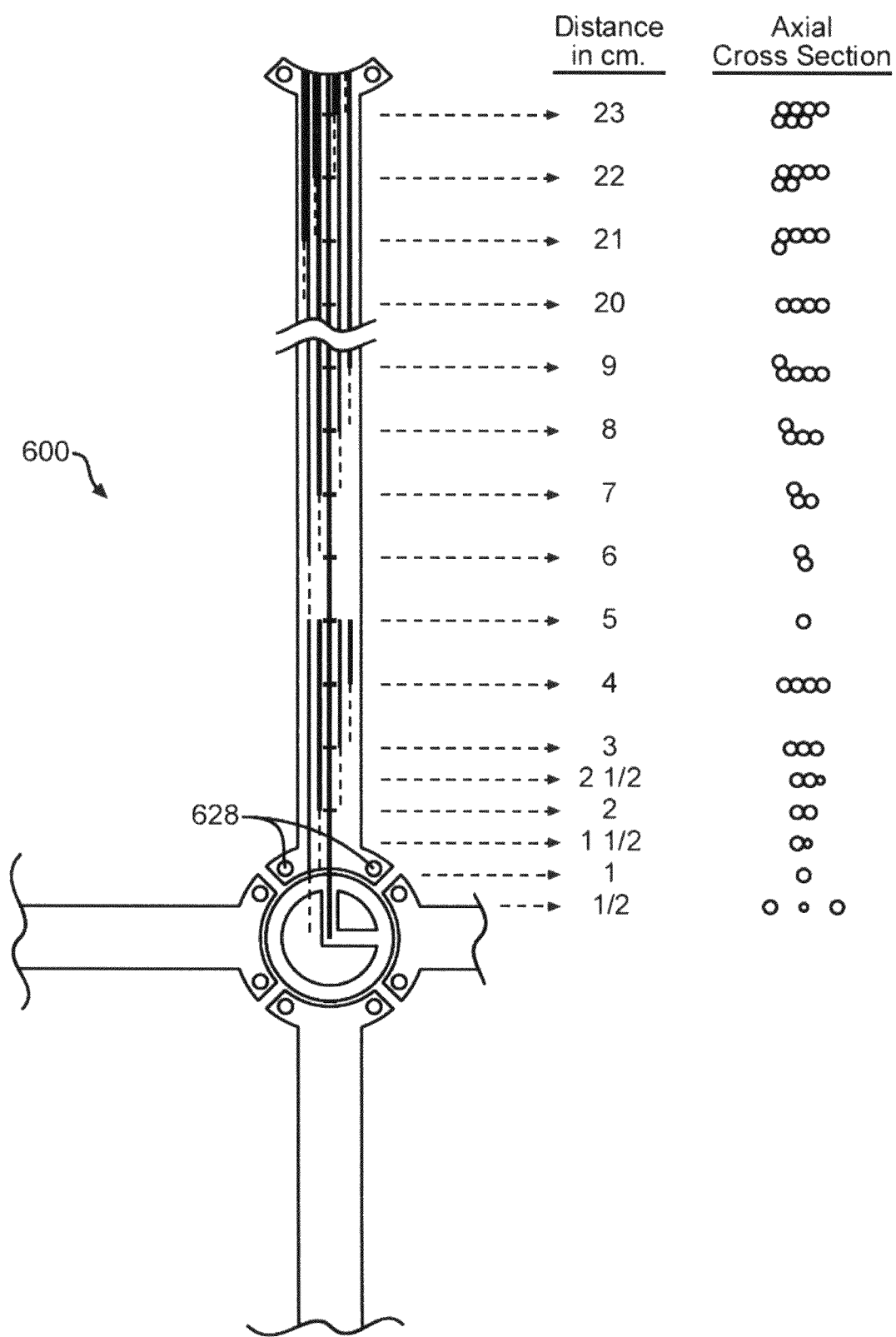
Figure 15E:
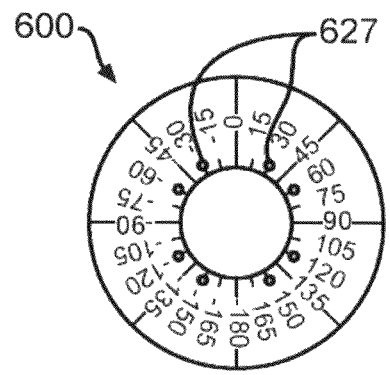
Figure 15F:
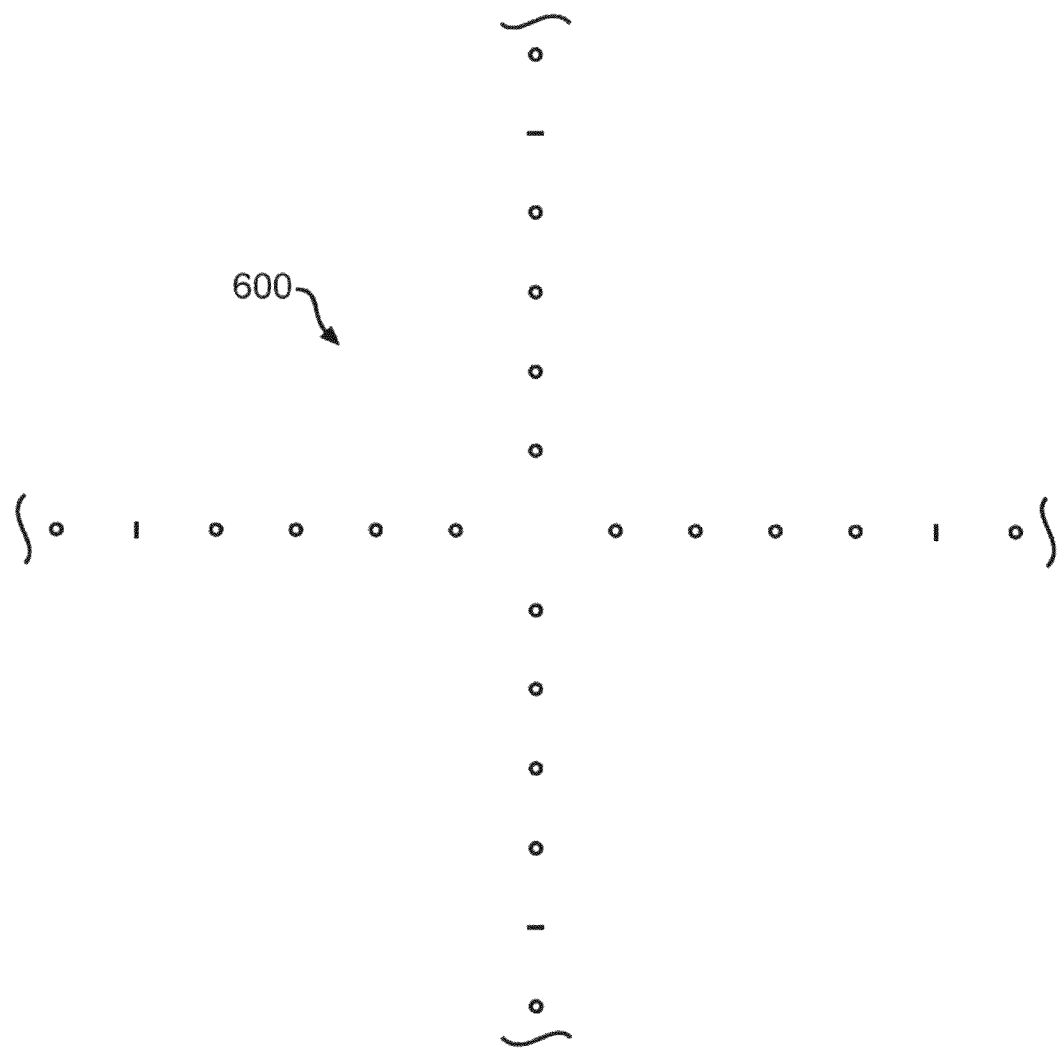

To add further utility and integration with the previously described point localizers, a modified ring may serve as the hub of the cross-shaped grid with associated modification of the limbs as illustrated in FIG. 15D. The orthogonal limbs would not have to maintain a coincident relationship to the spokes as with the modified square hub. Rather, by first placing and rotating a calibrated ring adapter (FIG. 15E) about the modified loop, 1 to 4 limbs could be readily positioned at any desired angle relative to the spokes. Pairs of male plugs 627 extending from the ring, adapter would fit securely into corresponding holes 628 at each limb base to ensure proper positioning. It is foreseen that one would typically align the modified ring's spokes with the scanner's axes and the ring adapter/limbs with the axes of the body part to be studied. By noting the chosen angulation marked on the ring adapter, optimal scanning planes might be determined prior to imaging.

For planar radiography, the detectable region might comprise a cross-shaped grid of radiopaque (e.g. lead or aluminum) dots at 1 cm intervals interposed by 5 cm spaced dashes (FIG. 15E) would minimize the imaging area obscured by overlying radiopacity. The minute opacities could be reversibly affixed by clear tape to an underlying marked adhesive fabric similar to that illustrated in FIG. 15C. Alternatively, in FIG. 15F similarly spaced radiopaque dots and dashes could be dispensed reversibly affixed to a role of medical grade adhesive tape with corresponding markings. Any length of this dually marked taped could be applied to the patient to include a single dot as a point localizer.

Figure 16A:
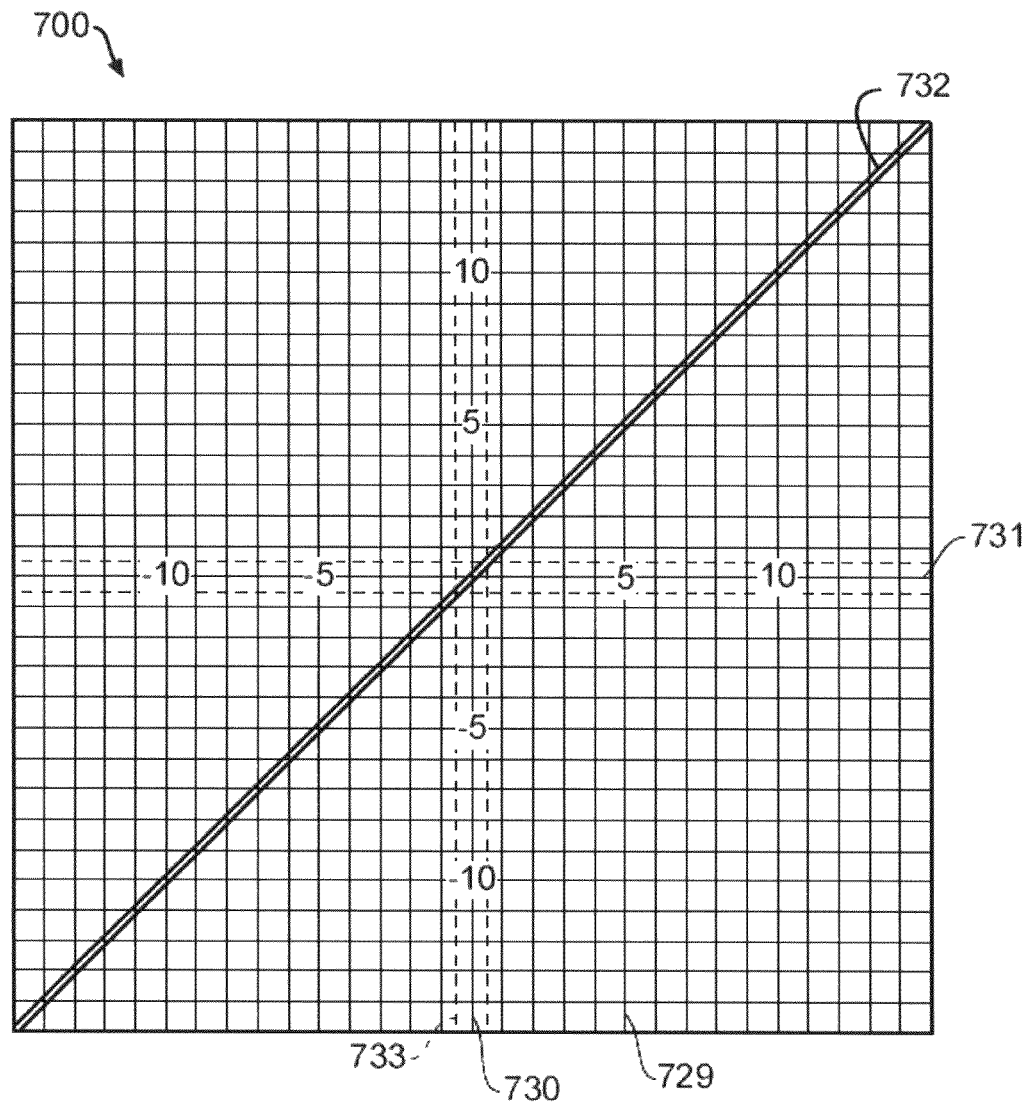
FIG. 16A is an enface view of the grid/phantom configuration with tubular lattice, overlying a diagonally oriented slice indicator, and underlying a partially adhesive fabric with markings and perforations.
Figure 16B:
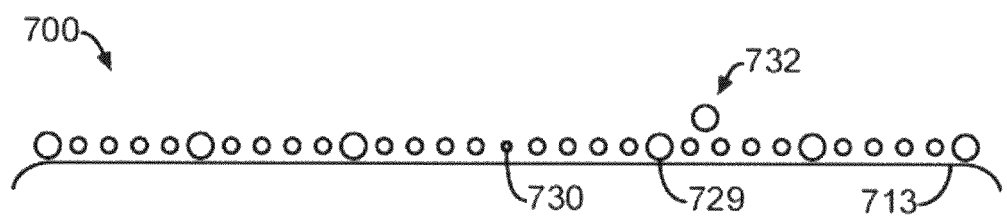
FIG. 16B is a schematic cross section of a representative axial section of the grid/phantom configuration of FIG. 16A.

In a planar localizer grid/phantom 700 such as shown in FIG. 16A, 1 cm spaced horizontal and vertical tubes can be combined to form a graph paper-like lattice as illustrated. In the illustrated configuration, tubes at 5 cm intervals (729) would have larger luminal diameters (e.g. 3 mm) than the others (e.g. 2 mm). Central vertical 730 and horizontal 731 tubes would have a smaller diameter (e.g. 1 mm). Overlying the lattice at a 45 degree angle is a slice indicator tube 732. Depending on the distance from the horizontal or vertical axes respectively, axial or sagittal cross sections through the grid/phantom (GP) would demonstrate the slice indicator tube 732 uniquely positioned as it overlies a row of 1 cm spaced tubes. FIG. 16B illustrates a representative axial slice obtained 6½ cm above the horizontal axis. Note that the cross section of the slice indicator is positioned above and midway between the sixth and seventh tubes to the right of the sectioned vertical axis 730. Additionally, the thickness (t) of the image section can be readily determined as it equals the cross-sectional width (w) of the indicator minus the square root of 2 times the diameter (d) of the indicator lumen, $(t=w-d\sqrt{2})$.

The GP may be reversibly affixed to an adhesive/plastic sheet 713 with a corresponding graph paper-like grid for skin marking and to serve as a sterile interface between the patient and GP. Perforations 733 may be placed in the sheet as shown in FIG. 16A to allow ready separation of a cross-like ruled adhesive fabric (similar to that illustrated in FIG. 15C), from the remaining plastic sheet after imaging and removal of the GP.

The square GP can preferably be constructed to have outer dimensions equal to a multiple of 10 cm (e.g. 30 cm as illustrated) to allow for simple computation if GPs are placed side to side for expanded surface coverage. Adapters could be provided to ensure secure and precise positioning of adjacent GPs either in plane or at right angles to each other. The GPs can be flexible or rigid in construction and be utilized with or without skin adhesion and marking.

Tubes may be filled uniformly or with a variety of known solutions having different imaging properties to serve as multipurpose references. For the latter, the 5 cm spaced tubes and slice indicator may be filled with the same optimized solution as previously described, while each set of 4 intervening tubes could be filled with different solutions in similar sequence. In this fashion, identical series of 5 reference solutions would repeat every 5 cm, allowing intraslice signal homogeneity to be assessed as well. If 9 rather than 5 different solutions are desired, sequences could instead be repeated every 10 cm. For MRI, the central tubes may also be surrounded by an oil/lipid within a larger lumen tube to serve as both a lipid signal reference and allow for measurement of the fat/water spatial chemical shift. Furthermore, if the GP tubing is surrounded by a perfluorocarbon or other substance without magnetic susceptibility, MR imaging could be improved by reducing skin/air susceptibility artifact and dampening motion. The GP may also be incorporated into a variety of nonmodality specific pads (including the ubiquitous scanner table pad(s)), binders, compression plates, biopsy grids and assorted stereotaxic devices.

Two additional variations are now described, potentially replacing the somewhat complex cross design (FIGS. 15A-15F) with an extension of the basic point localizer (FIGS. 14A-14I) or modification of the planar phantom/localizer (FIGS. 16A-16B). These changes may further simplify and unify the proposed marking system.

Figure 17A:
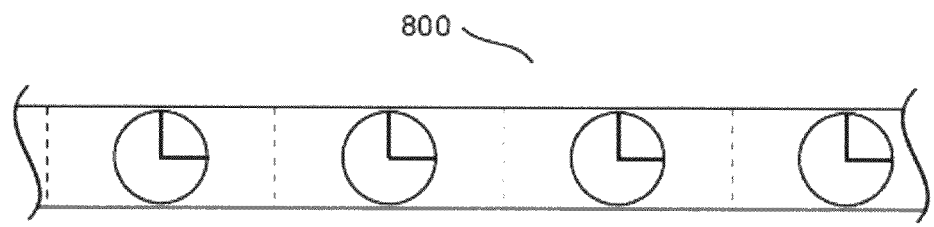
FIGS. 17A-17B are diagrams of localizers in a packaged strip or roll, regularly spaced at 5 cm or other intervals.
Figure 17B:
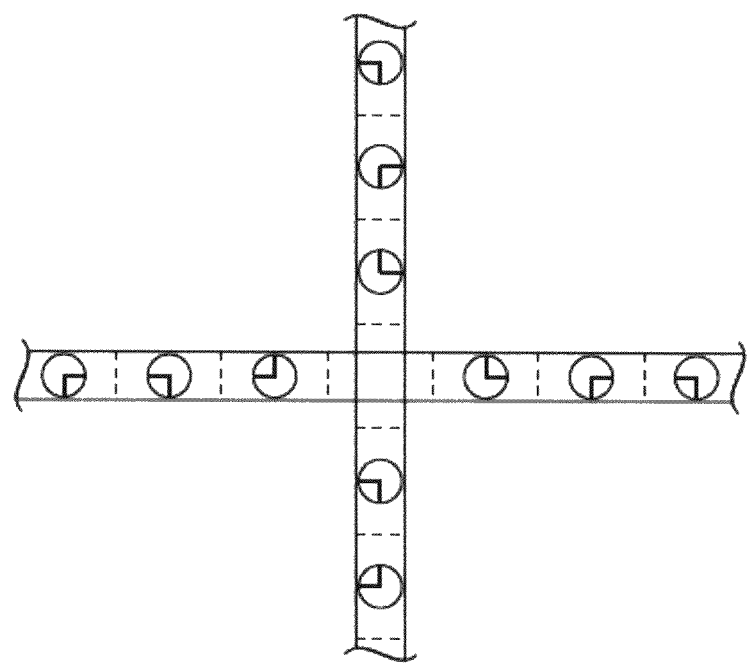

In the first instance, rather than packaging the ring localizers in a sheet as illustrated in FIG. 14I, they could be packaged in a strip or roll 800, regularly spaced at 5 cm or other intervals (FIG. 17A). The strip 800 with attached ring and/or cross localizers could then serve as a linear reference of any desired length. By placing two strips orthogonally, a cross-shaped grid is created (FIG. 17B). Individual rings can be removed from the strip or rotated to customize the grid as desired.

In the second instance, by slightly modifying the square design illustrated in FIGS. 16A-16B, an elongated rectilinear or cross configuration (FIG. 18A) is achieved consisting of linearly arranged squares extending vertically and/or horizontally from the central square. One tube in each of these squares will have a larger diameter than the other similarly oriented tubes as determined by the square's distance from the isocenter. For example, the square centered 10 cm above the isocenter would have its first tube situated to the right of midline given an increased diameter and the square centered 20 cm above the isocenter would have its second tube to the right of midline given an increased diameter and so on.

Figures 18A, 18B:
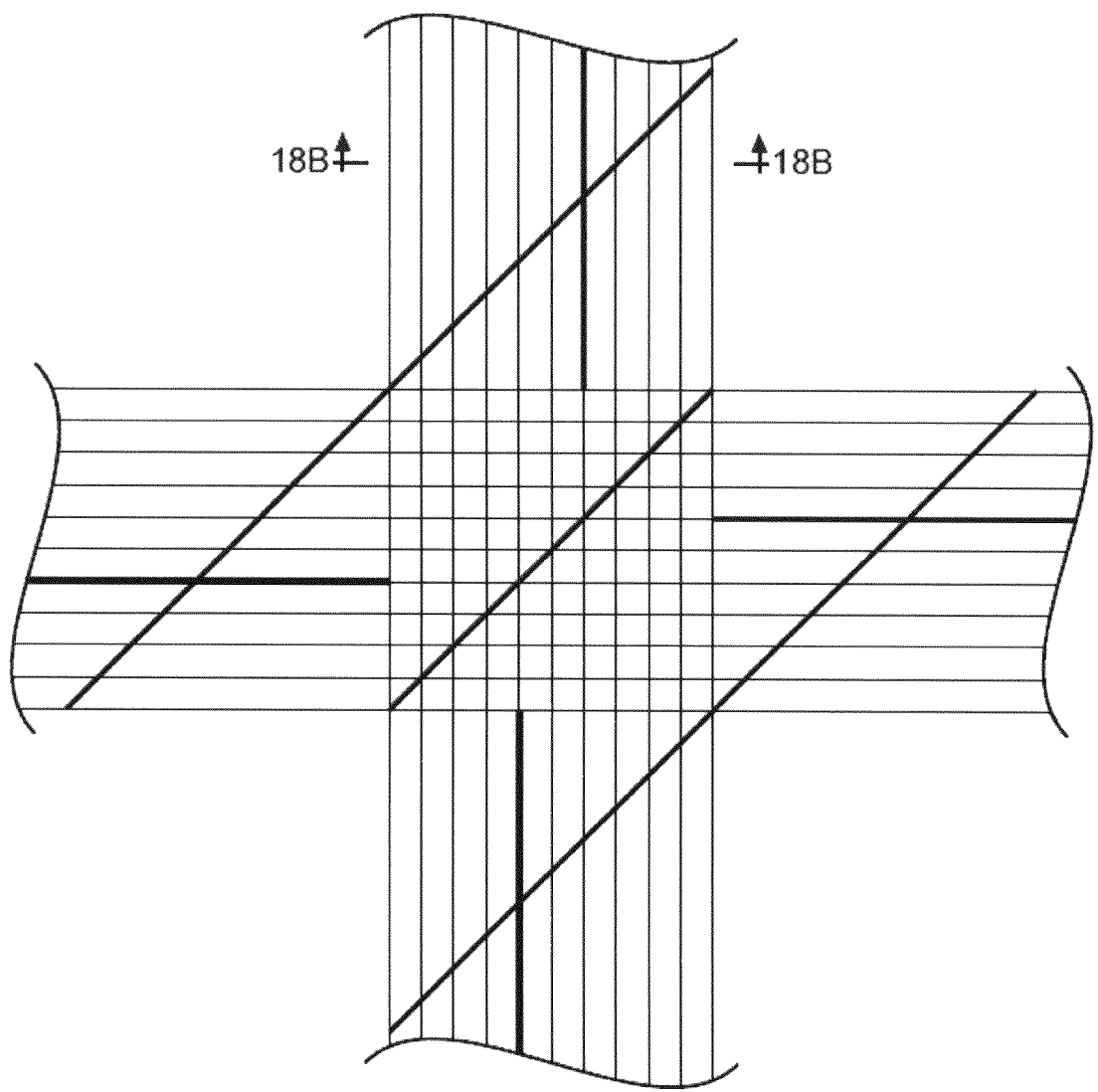
FIGS. 18A-18B are depictions of a lattice localizer having tube diameters varied to identify unique locations.

Cross sectional distance from isocenter would be read by adding the distance determined by each square's diagonally oriented slice indicator to 10 times the numberline position of the largest diameter tube. FIG. 18B illustrates the cross sectional appearance of an axial section obtained 12½ cm. above isocenter. By adding 2½ (the slice indicator position) to 10 times 1 (the tube with largest diameter), distance is readily determined.

Alternatively, the caliber of all tubes could be kept constant and instead an additional diagonal indicator tube passing through isocenter added for each elongated axis (vertical with slope of 10 and horizontal with slope of 1/10). Cross-sectional distance from isocenter would then be determined by looking at the position of both the additional and original diagonal indicator tubes in reference to the cross sectionally-created number line.

It should also be noted that localizer grids similar to those illustrated in FIGS. 16A-16B and 18A-18B could be constructed of barium (or other high x-ray attenuative material) impregnated sheets rather than tubes if computed tomography is the primary imaging modality desired and phantom attenuation values are not needed. This would significantly reduce the cost of the grid, allowing disposability and retaining 1:1 compatibility with the multifunctional tube filled grid/phantom.

Figure 19A:
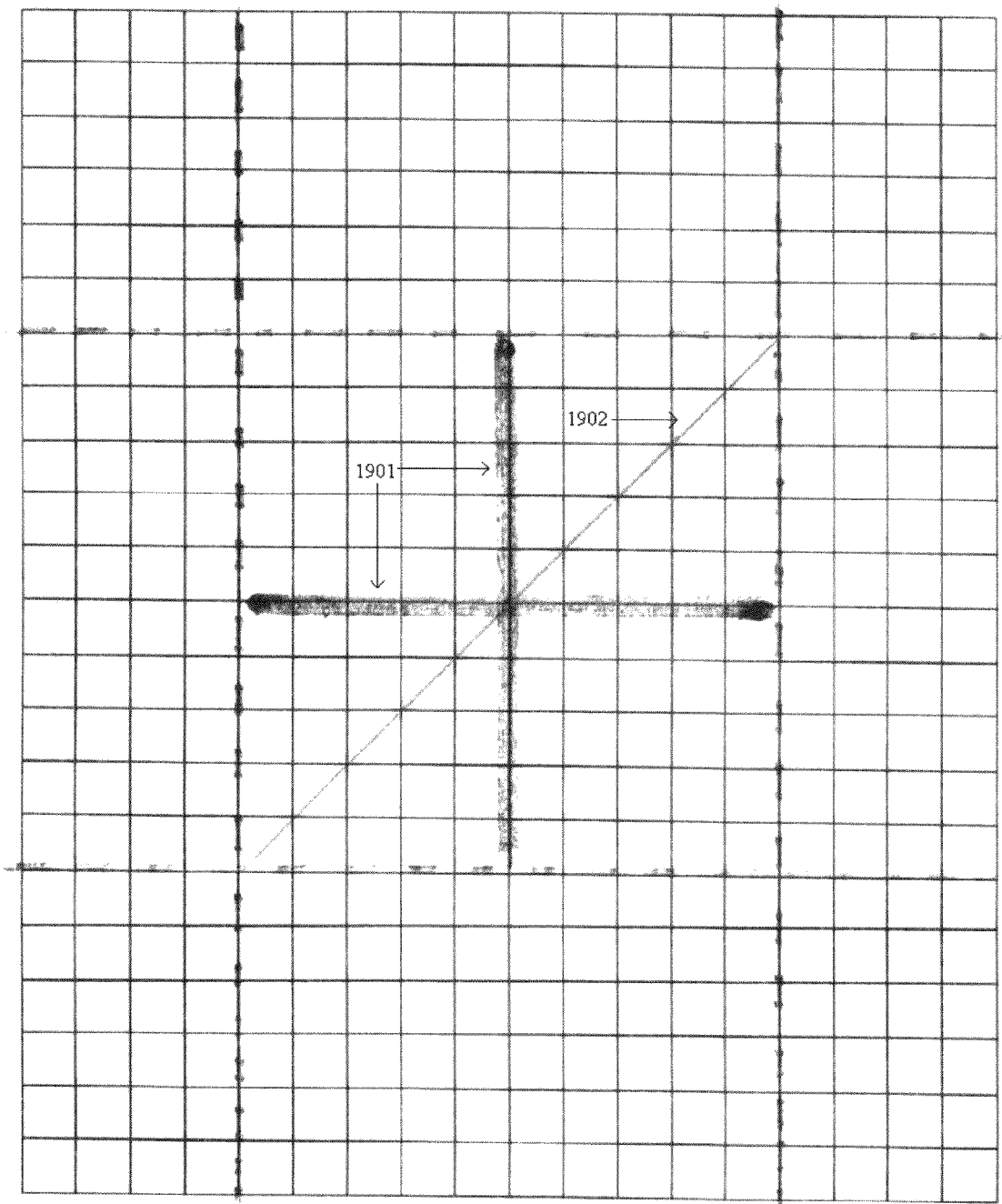
FIG. 19A depicts a cross localizer having two central tubes and a crossing tube.

Yet another approach to the implementation of a localizer is to manufacture a localizer in either 10 cm×10×cm strips with perforations at 10 cm intervals or as sheets containing multiple 10 cm2 grids (e.g. a 30×30 cm sheet would contain 9 grids), as shown in FIG. 19A. In such a case, each individual grid could consist of three tubes (which should be understood to include not only cylindrical tubes, but also flattened areas where radiopaque material might be inserted, elongated ovoids, and other tube-like structures). Two central tubes [1901] measuring less than or equal to 10 cm in length would form a cross configuration, whereas a third tube [1902] (which might be distinguishable from the central tubes by, for example, color, diameter, shape, or other characteristic) could pass diagonally through the center and measure 10×sq root 2 or less in length. Alternatively, instead of the tubes [1901] [1902] intersecting, the localizer could be constructed so that the tubes do not cover the point where they would otherwise intersect (FIG. 19D). A single or multiple grids could be placed or affixed to the patient's skin surface as previously described. If desired, the grid could be aligned with the spatial system of the cross sectional imaging apparatus utilized; for example some systems have a laser light system that projects a center point or cross on the patient to be scanned.

Figure 19B:
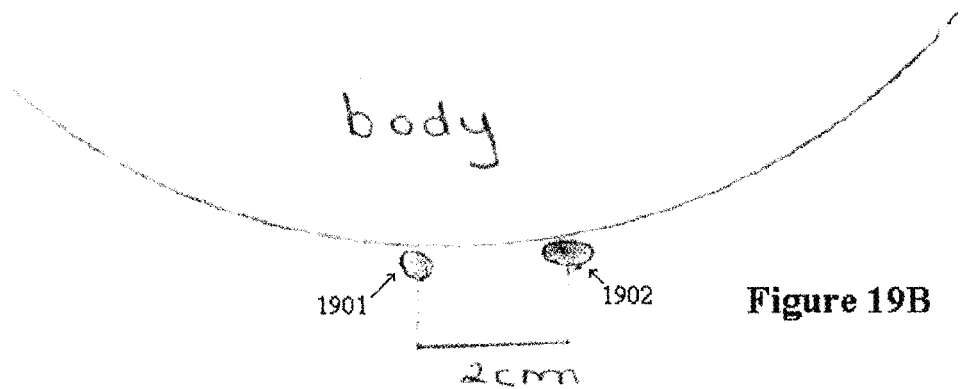
FIGS. 19B-19C depict the cross localizer of FIG. 19A as it may be applied to a patient's skin and as it may appear on a cross sectional imaging study.
Figure 19C:
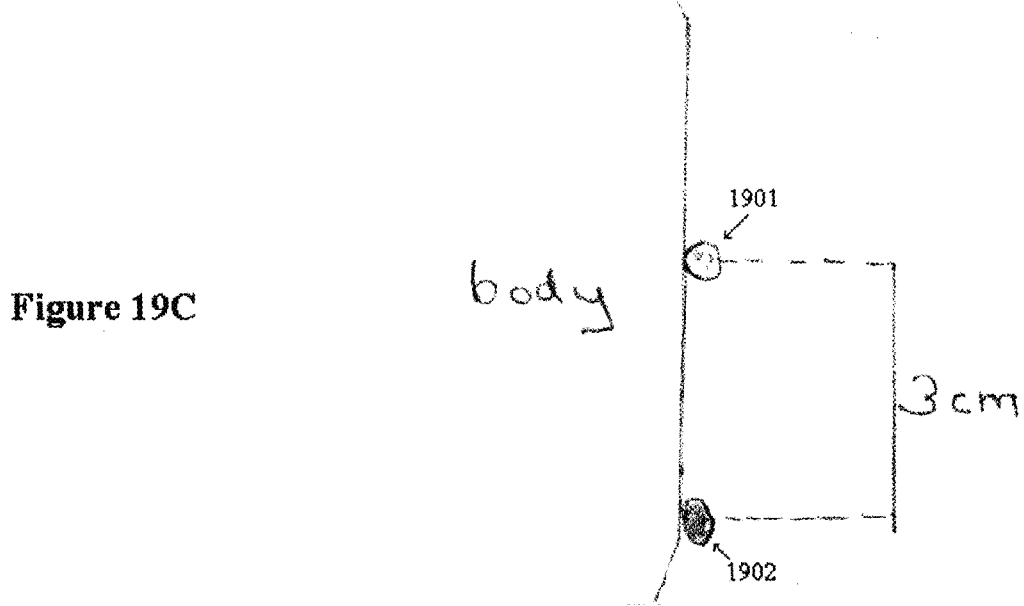
Figure 19D:
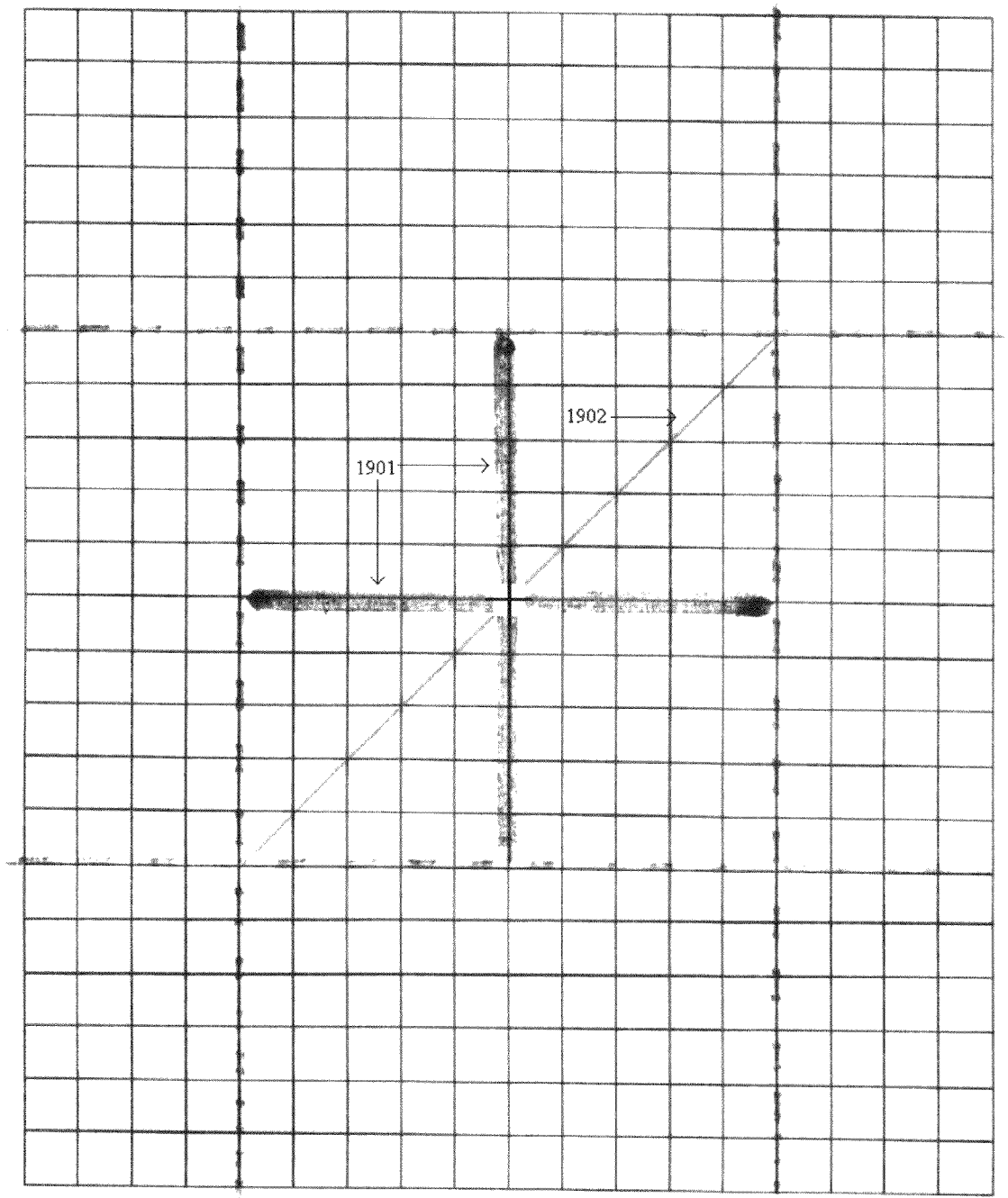
FIG. 19D depicts a cross localizer having central tubes and a crossing tube where the tubes do not encroach onto the intersection point.

With grid in place, the position of axial or sagittal sections or reformations relative to the patient can be readily derived by measuring the distance between two a central and a crossing tube [1901] [1902] seen in cross section on the patient's skin surface in FIGS. 19B and 19C. With the grid configuration described, on sagittal images, x (abscissa)=positive or negative y (ordinate) distance; whereas on axial images, y=positive or negative x distance. If no markers are visualized and the region of interest is covered by contiguous grids, then the x or y position would be at 5+10a cm from the isocenter, where (a) is a positive or negative integer; and the section would be pass through the perforations (dashed lines).

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer apparatus comprising:
    (a) a non-transitory memory configured to receive one or more medical diagnostic images;
    (b) a program stored in the non-transitory memory and operatively configured to detect and label at least one spinal structure in said medical diagnostic images; and
    (c) a computer processor in communication with the non-transitory memory and configured to perform the program by executing computer executable instructions, wherein the program is operatively configured to automatically generate a prescription using said labeling.

2. The apparatus of claim 1 wherein said labeling is used to label similar structures in additional medical diagnostic images of the same individual.

3. The apparatus of claim 1 wherein said labeling is used to guide a therapeutic procedure.

4. The apparatus of claim 1 wherein said labeling is used in the segmentation of one or more spinal structures.

5. The apparatus of claim 1 wherein the program is further operatively configured to make quantitative measurements related to labeled structures or their relationships to each other.

6. The apparatus of claim 1 wherein said labeling is used to assess for possible abnormalities.

7. The apparatus of claim 1 wherein the medical diagnostic images are obtained at least in part from a picture archiving system.

8. The apparatus of claim 1 wherein said labeling is used to compare similarly labeled structures in a plurality of medical diagnostic images of the same individual.

9. The apparatus of claim 1 wherein said labeling uses the C1-C7, T1-T12, L1-L5 and S1-S5 convention.

10. The apparatus of claim 1, wherein the prescription is to prescribe image reformations.

11. An apparatus for accurately labeling spinal related structures even in the presence of anatomic variation, comprising:
    (a) one or more computer processors;
    (b) a non-transitory memory configured to receive medical diagnostic images;
    (c) a program comprising computer executable instructions stored in the non-transitory memory that upon being executed by the one or more computer processors performs a method comprising:
        providing a set of one or more medical diagnostic images for a particular individual, wherein at least one of the medical diagnostic images includes a plurality of non-cervical spinal-related structures to be labeled;
        identifying a uniquely identifiable high cervical structure cranial to the C4 vertebra in the set of one or more medical diagnostic images; and
        deriving a label for the plurality of non-cervical spinal-related structures in the at least one medical diagnostic images based at least in part on the identified unique high cervical structure.

12. The apparatus of claim 11, wherein the unique high cervical structure includes the C1 vertebra or the C2 vertebra.

13. The apparatus of claim 11, wherein the unique high cervical structure includes the C2-C3 inter-vertebral disc or the C3 vertebra.

14. The apparatus of claim 11, wherein the method further comprises identifying a chain of structures extending from the high cervical structure to the plurality of non-cervical structures.

15. The apparatus of claim 14, wherein the chain of structures includes one or more intervertebral discs, one or more vertebrae, one or more spine related structures identified in a cranial caudal direction, the spinal canal, the spinal cord, the skin surface, or a combination thereof.

16. The apparatus of claim 11, wherein the method further comprises identifying a second structure selected from the spinal cord, spinal canal, skin surface, or combination thereof.

17. The apparatus of claim 11, wherein the method further comprises identifying one or more structures in the set of one or more images using fat-water decomposition.

18. The apparatus of claim 11, wherein the at least one medical diagnostic image includes a midline sagittal image generated from volumetric imaging data.

19. The apparatus of claim 18, wherein the midline sagittal image includes a curved oblique reference to the spinal axis along the spine's plane of symmetry.

20. The apparatus of claim 11, further comprising identifying an abnormality in non-cervical spinal-related structures.

21. The apparatus of claim 11, wherein the non-cervical spinal-related structures include one or more thoracic vertebra, one or more thoracic inter-vertebral discs, or a combination thereof.

22. The apparatus of claim 11, wherein the non-cervical spinal-related structures include one or more lumbar vertebrae, one or more lumbar inter-vertebral discs, or a combination thereof.

23. The apparatus of claim 11, wherein the non-cervical spinal-related structures include one or more ribs, the sacrum, or a combination thereof.

24. The apparatus of claim 11 wherein the set of one or more images includes at least two images, the first image including the high cervical structure and the second image including the non-cervical spinal-related structures.

25. The apparatus of claim 11 wherein the labeling is used to compare corresponding structures between two or more images in the set of one or more diagnostic images.

26. The apparatus of claim 11 wherein the labeling is used to guide a therapeutic procedure.

27. The apparatus of claim 11 wherein the labeling is used in the segmentation of the plurality of spinal-related structures.

28. The apparatus of claim 11 wherein the program is further operatively configured to make quantitative measurements related to labeled non-cervical spinal-related structures or their relationships to each other.

29. The apparatus of claim 11 wherein the first medical diagnostic image is obtained at least in part from a picture archiving system.

30. The apparatus of claim 11, where the plurality of spinal-related structures are iteratively detected and labeled in a cranial to caudal manner.

31. The apparatus of claim 11 wherein the program is operatively configured to provide a diagnostic report.

32. The apparatus of claim 11, wherein the identification of the plurality of spinal-related structures uses a detection algorithm that is constrained in part on information available in a DICOM header.

33. The apparatus of claim 32, wherein said information available in the DICOM header includes one or more of the following factors: an individual's age, an individual's gender, an individual's weight, or a combination of the foregoing.

* * * * *